(12) United States Patent
Mietus et al.

(10) Patent No.: US 7,734,334 B2
(45) Date of Patent: Jun. 8, 2010

(54) ASSESSMENT OF SLEEP QUALITY AND SLEEP DISORDERED BREATHING BASED ON CARDIOPULMONARY COUPLING

(75) Inventors: Joseph E. Mietus, Cambridge, MA (US); Chung-Kang Peng, Sharon, MA (US); Robert J. Thomas, Newton, MA (US); Ary L. Goldberger, Newton Centre, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 1296 days.

(21) Appl. No.: 11/178,990

(22) Filed: Jul. 12, 2005

(65) Prior Publication Data

US 2005/0267362 A1    Dec. 1, 2005

Related U.S. Application Data

(63) Continuation-in-part of application No. 10/846,945, filed on May 17, 2004, now Pat. No. 7,324,845.

(51) Int. Cl.
*A61B 5/04*        (2006.01)

(52) U.S. Cl. .................. 600/513; 600/484; 600/534; 600/536

(58) Field of Classification Search .............. 600/481, 600/484, 301, 513, 534–536
See application file for complete search history.

(56) References Cited

U.S. PATENT DOCUMENTS

| | | | |
|---|---|---|---|
| 5,105,354 A | 4/1992 | Nishimura | |
| 5,902,250 A | 5/1999 | Verrier et al. | |
| 6,415,174 B1 | 7/2002 | Bebehani et al. | |
| 6,739,335 B1 * | 5/2004 | Rapport et al. | 128/204.18 |
| 7,179,229 B1 * | 2/2007 | Koh | 600/485 |

(Continued)

FOREIGN PATENT DOCUMENTS

WO        WO 98/43536        10/1998

OTHER PUBLICATIONS

Supplemental European Search Report for European Application No. EP 05 74 9482, European Patent Office, search completed: Jun. 19, 2009, 3 pgs.

(Continued)

*Primary Examiner*—Mark W Bockelman
(74) *Attorney, Agent, or Firm*—Sterne, Kessler, Goldstein & Fox P.L.L.C.

(57) ABSTRACT

An assessment of sleep quality and sleep disordered breathing is determined from cardiopulmonary coupling between two physiological data series. An R-R interval series is derived from an electrocardiogram (ECG) signal. The normal beats from the R-R interval series are extracted to produce a normal-to-normal interval series. The amplitude variations in the QRS complex are used to extract a surrogate respiration signal (i.e., ECG-derived respiration) associated with the NN interval series. The two series are corrected to remove outliers, and resampled. The cross-spectral power and coherence of the two resampled signals are calculated over a plurality of coherence windows. For each coherence window, the product of the coherence and cross-spectral power is used to calculate coherent cross-power. Using the appropriate thresholds for the coherent cross-power, the proportion of sleep spent in CAP, non-CAP, and wake and/or REM are determined. Coherent cross-power can be applied to differentiate obstructive from non-obstructive disease, and admixtures of the same.

13 Claims, 11 Drawing Sheets

U.S. PATENT DOCUMENTS

2003/0055348 A1  3/2003  Chazal et al.
2005/0256418 A1  11/2005  Mietus et al.

OTHER PUBLICATIONS

Raymond B. et al., "Screening for Obstructive Sleep Apnoea Based on the Electrocardiogram—The Computer in Cardiology Challenge" *Computers in Cardiology*, vol. 27, pp. 267-270 (2000).
Redmond S. et al., "Electrocardiogram-Based Automatic Sleep Staging in Sleep Disordered Breathing" *Computers in Cardiology*, vol. 30, pp. 609-612 (2003).
Unbehaun A. et al., "Interaction of heart-rate fluctuations and respiration in 12 to 14-year-old children during sleeping and waking" *Journal of the Autonomic Nervous System*, vol. 57, pp. 141-143 (1996).
Aljadeff, G. et al., "Heart Rate Variability in Children With Obstructive Sleep Apnea," *Sleep*, vol. 20, No. 2, pp. 151-157 (Feb. 1997).
Benitez, D. et al., "The use of the Hilbert transform in ECG signal analysis," *Computers in Biology and Medicine*, vol. 31, pp. 399-406 (2001).
Blasi, A. et al., "Cardiovascular variability after arousal from sleep: time-varying spectral analysis," *Journal of Applied Physiology*, vol. 95, No. 4, pp. 1394-1404 (Oct. 2003).
Boland, L.L. et al., "Measures of cognitive function in persons with varying degrees of sleep-disordered breathing: the Sleep Heart Health Study," *Journal of Sleep Research*, vol. 11, pp. 265-272 (2002).
Buchheit, M. et al., "Effect of increased training load on vagal-related indexes of heart rate variability: a novel sleep approach," *American Journal of Physiology*, vol. 287, No. 6, Part 2, pp. H2813-H2818 (Dec. 2004).
Carter, N. et al., "Cardiovascular and Autonomic Response to Environmental Noise During Sleep in Night Shift Workers," *Sleep*, vol. 25, No. 4, pp. 457-464 (Jun. 15, 2002).
Chervin, R.D. and Aldrich, M.S., "The Relation Between Multiple Sleep Latency Test Findings and the Frequency of Apneic Events in REM and Non-REM Sleep," *Chest*, vol. 113, No. 4, pp. 980-984 (Apr. 1998).
Chervin, R.D. et al., "Inattention, Hyperactivity, and Symptoms of Sleep-Disordered Breathing," *Pedriatics*, vol. 109, No. 3, pp. 449-456 (Mar. 2002).
Chesson, A.L. Jr. et al., "The Indications for Polysomnography and Related Procedures," *Sleep*, vol. 20, No. 6, pp. 423-487 (Jun. 1997).
Cohen, J., *Statistical Power Analysis for the Behavioral Sciences*, 2nd ed, Lawrence Erlbaum Associates, Hillsdale, NJ, pp. vii-ix, xi-xv, xvii-xxi, 1-17, and 559-567 (1988).
Collop, N.A., "Scoring variability between polysomnography technologists in different sleep laboratories," *Sleep Medicine*, vol. 3, pp. 43-47 (2002).
Cornolo, J. et al., "Autonomic control of the cardiovascular system during acclimatization to high altitude: effects fo sildenafil," *Journal of Applied Physiology*, vol. 97, No. 3, pp. 935-940 (Sep. 2004).
de Chazal, P. et al., "Automated Processing of the Single-Lead Electrocardiogram for the Detection of Obstructive Sleep Apnoea," *IEEE Transactions on Biomedical Engineering*, vol. 50, No. 6, pp. 686-696 (Jun. 2003).
De Gennaro, L. et al., "The Cyclic Alternating Pattern Decreases as a Consequence of Total Sleep Deprivation and Correlates with EEG Arousals," *Neurpsychobiology*, vol. 45, No. 2, pp. 95-98 (Mar. 2002).
Dingli, K. et al., "Spectral oscillations of RR intervals in sleep aponea/hypopnoea syndrome patients," *European Respiratory Journal*, vol. 22, No. 6, pp. 943-950 (Dec. 2003).
Dumont, M. et al., "Interdependency between heart rate variability and sleep EEG: linear/non-linear?," *Clinical Neurophysiology*, vol. 115, No. 9, pp. 2031-2040 (May 18, 2004).
Dworschak, M. et al., "The use of spectral measures of heart rate variability to differentiate between male snorers and patients with sleep apnoea syndrome," *Anaesthesia*, vol. 56, No. 5, pp. 424-428 (May 2001).

Engleman, H.M. et al., "Cognitive Function in the Sleep Apnea/Hypopnea Syndrome (SAHS)," *Sleep*, vol. 23, Supplement 4, pp. S102-S108 (Jun. 15, 2000).
Farina, B. et al., "Microstructure of sleep in depressed patients according to the cyclic alternating pattern," *Journal of Affective Disorders*, vol. 77, Issue 3, pp. 227-235 (Dec. 2003).
Ferini-Strambi, L. et al., "The impact of cyclic alternating pattern on heart rate variability during sleep in healthy young adults," *Clinical Neurophysiology*, vol. 111, pp. 99-101 (2000).
Ferini-Strambi, L. et al., "Heart Rate Variability during Sleep in Snorers with and without Obstructive Sleep Apnea," *Chest*, vol. 102, No. 4, pp. 1023-1027 (Oct. 1992).
Goldberger, A.L. et al., "PhysioBank, PhysioToolkit, and PhysioNet: Components of a New Research Resource for Complex Physiological Signals," *Circulation*, pp. 1-6 (Jun. 13, 2000).
Gottlieb, D. J. et al., "Symptoms of Sleep-Disordered Breathing in 5-Year-Old Children Are Associated With Sleepiness and Problem Behaviors," *Pediatrics*, vol. 112, No. 4, pp. 870-877 (Oct. 2003).
Gottlieb D,J. et al., "Does Snoring Predict Sleepiness Independently of Apnea And Hypopnea Frequency?" *American Journal of Respiratory and Critical Care Medicine*, vol. 162, No. 4, pp. 1512-1517 (Oct. 2000).
Gottlieb, D.J. et al., "Relation of Sleepiness to Respiratory Disturbance Index: The Sleep Heart Health Study," *American Journal of Respiratory and Critical Care Medicine*, vol. 159, No. 2, pp. 502-507 (Feb. 1999).
Gozal, D. "Sleep-Disordered Breathing and School Performance in Children," *Pediatrics*, vol. 102, No. 3, Part 1, pp. 616-620 (Sep. 1998).
Greene, M.G. and Carroll, J.L., "Consequences of Sleep-disordered breathing in childhood," *Current Opinion in Pulmonary Medicine*, vol. 3, No. 6, pp. 456-463 (Nov. 1997).
Guilleminault, C. et al., "Cyclical Variation Of The Heart Rate In Sleep Apnoea Syndrome: Mechanisms, and Usefulness of 24 h Electrocardiography as a Screening Technique," *The Lancet*, vol. I, No. 8369, pp. 126-131 (Jan. 21, 1984).
Gula , L.J. et al., "Heart Rate Variability in Obstructive Sleep Apnea: A Prospective Study and Frequency Domain Analysis," *A.N.E.*, vol. 8, No. 2, pp. 144-149 (Apr. 2003).
Halász, P. et al., "The nature of arousal in sleep," *Journal of Sleep Research*, vol. 13, pp. 1-23 (2004).
Hilton, M.F. et al., "Evaluation of frequency and time-frequency spectral analysis of heart rate variability as a diagnostic marker of the sleep apnoea syndrome," *Medical & Biological Engineering & Computing*, vol. 37, No. 6, pp. 760-769 (Nov. 1999).
Iellamo, F. et al., "Baroreflex Buffering of Sympathetic Activation During Sleep: Evidence From Autonomic Assessment of Sleep Macroarchitecture and Microarchitecture," *Hypertension*, vol. 43, No. 4, pp. 814-819 (Apr. 2004).
Khoo, M.C.K. et al., "Spectral Indices of Cardiac Autonomic Function in Obstructive Sleep Apnea," *Sleep*, vol. 22, No. 4, pp. 443-451 (Jun. 15, 1999).
Kingshott, R.N. et al., "Does arousal frequency predict daytime function?," *European Respiratory Journal*, vol. 12, No. 6, pp. 1264-1270 (Dec. 1998).
Kuo, T.B., "Scatterplot Analysis of EEG Slow-Wave Magnitude and Heart Rate Variability: An Integrative Exploration of Cerebral Cortical and Autonomic Functions," *Sleep*, vol. 27, No. 4, pp. 648-656 (Jun. 15, 2004).
Lieberman, H.R. et al., "Effect of caffeine, sleep loss, and stress on cognitive performance and mood during U.S. Navy SEAL training," *Psychopharmacology*, vol. 164, pp. 250-261 (2002).
Lipsitz, L.A. et al., "Heart rate and respiratory rhythm dynamics on ascent to high altitude," *British Heart Journal*, vol. 74, No. 4, pp. 390-396 (Oct. 1995).
Lord, S. et al., "Interrater Reliability of Computer-Assisted Scoring of Breathing during Sleep," *Sleep*, vol. 12, No. 6, pp. 550-558 (Dec. 1989).
Manser, R.L. et al., "Impact of Different Criteria for Defining Hypopneas in the Apnea-Hypopnea Index," *Chest*, vol. 120, No. 3, pp. 909-914 (Sep. 2001).

Margel, D. et al., "Long-Term Intermittent Exposure to High Ambient $CO_2$ Causes Respiratory Disturbances During Sleep in Submariners," *Chest*, vol. 124, No. 5, pp. 1716-1723 (Nov. 2003).
Mark, R.G. and Moody, G.B., "Arrhythmia Analysis, Automated," *Encyclopedia of Medical Devices and Instrumentation*, vol. 1, pp. 120-130 (1988).
Mendelson, W.B., "The Relationship of Sleepiness and Blood Pressure to Respiratory Variables in Obstructive Sleep Apnea," *Chest*, vol. 108, No. 4, pp. 966-972 (Oct. 1995).
Meoli, A.L. et al., "Hypopnea in Sleep-Disordered Breathing in Adults," *Sleep*, vol. 24, No. 4, pp. 469-470 (Jun. 15, 2001).
Mietus, J.E. et al., "Detection of Obstructive Sleep Apnea from Cardiac Interbeat Interval Time Series," *Computers in Cardiology*, vol. 27, pp. 753-756 (Sep. 24-27, 2000).
Mietus, J.E. et al., "The pNNx-files: re-examining a widely-used heart rate variability measure," *Heart*, vol. 88, No. 4, pp. 378-380 (Oct. 2002).
Miyashita, T. et al., "Spectral analyses of electroencephalography and heart rate variability during sleep in normal subjects," *Autonomic Neuroscience: Basic and Clinical*, vol. 103, pp. 114-120 (2003).
Moldofsky, H., "Management of sleep disorders in fibromyalgia," *Rheumatic Disease Clinics of North America*, vol. 28, No. 2, pp. 353-365 (May 2002).
Moody, G.B. and Mark, R.G., "Development and Evaluation of a 2-Lead ECG Analysis Program," *Computers in Cardiology*, pp. 39-44 (Oct. 12-15, 1982).
Moody, G.B. et al., "Clinical Validation Of the ECG-Derived Respiration (EDR) Technique," *Computers in Cardiology*, pp. 507-510 (Oct. 7-10, 1986).
Moody, G.B. et al., "Derivation Of Respiratory Signals From Multi-Lead ECGs," *Computers in Cardiology*, pp. 113-116 (Sep. 8-11, 1985).
Park, H.J. et al., "Automated Detection and Elimination of Periodic ECG Artifacts in EEG Using the Energy Interval Histogram Method," *IEEE Transactions on Biomedical Engineering*, vol. 49, No. 12, pp. 1526-1533 (Dec. 2002).
Parrino, L. at al., "Cyclic alternating pattern (CAP) in normal sleep: polysomnographic parameters in different age groups," *Electroencephalography and Clinical Neurophysiology*, vol. 107, No. 6, pp. 439-450 (Dec. 1998).
Parrino, L. et al., "Effects of prolonged wakefulness on cyclic alternating pattern (CAP) during sleep recovery at different circadian phases," *Journal of Sleep Research*, vol. 2, pp. 91-95 (1993).
Parrino, L. et al., "Is insomnia a neurophysiological disorder? The role of sleep EEG microstructure," *Brain Research Bulletin*, vol. 63, No. 5, pp. 377-383 (Jun. 30, 2004)
Parrino, L. et al., "Multidrug Comparison (Lorazepam, Triazolam, Zolpidem, and Zopiclone) in Situational Insomnia: Polysomnographic Analysis by Means of the Cyclic Alternating Pattern," *Clinical Neuropharmacology*, vol. 20, No. 3, pp. 253-263 (Jun. 1997).
Parrino, L. et al., "Sleep reactivity during acute nasal CPAP in obstructive sleep apnea syndrome," *Neurology*, vol. 54, No. 8, pp. 1633-1640 (Apr. 25, 2000).
Peled, N. et al., "Contributions of Hypoxia and Respiratory Disturbance Index to Sympathetic Activation and Blood Pressure in Obstructive Sleep Apnea Syndrome," *American Journal of Hypertension*, vol. 11, No. 11, Part 1, pp. 1284-1289 (Nov. 1998).
Penzel, T., "Is heart rate variability the simple solution to diagnose sleep apnoea?" *European Respiratory Journal*, vol. 22, pp. 870-871 (2003).
Penzel, T. et al., "Comparison of Detrended Fluctuation Analysis and Spectral Analysis for Heart Rate Variability in Sleep and Sleep Apnea," *IEEE Transactions on Biomedical Engineering*, vol. 50, No. 10, pp. 1143-1151 (Oct. 2003).
Penzel, T. et al., "Dynamics of Heart Rate and Sleep Stages in Normals and Patients with Sleep Apnea," *Neuropsychopharmacology*, vol. 28, Suppl. 1, pp. S48-S53 (Jul. 2003).
Penzel, T. et al., "Systematic comparison of different algorithms for apnoea detection based on electrocardiogram recordings," *Medical & Biological Engineering & Computing*, vol. 40, No. 4, pp. 402-407 (Apr. 2002).
"Practice Parameters for the Indications for Polysomnography and Related Procedures," *Sleep*, vol. 20, No. 6, pp. 406-422 (Jun. 1997).
Raschke, F., "Arousals and Aircraft Noise—Environmental Disorders of Sleep and Health in Terms of Sleep Medicine," *Noise Health*, vol. 6, pp. 15-26 (2004).
Rechtschaffen, A. and Kales, A. (eds.), *A Manual of standardized terminiology, techniques and scoring system for sleep stages of human subjects*, UCLA Brain Information Service, pp. 1-14 (1968).
Redline, S. et al., "the Effect of Age, Sex, Ethnicity, and Sleep-Disordered Breathing on Sleep Architecture," *Archives of Internal Medicine*, vol. 164, pp. 406-418 (Feb. 23, 2004).
Rizzi, M. et al., "Cyclic Alternating Pattern: A New Marker of Sleep Alteration in Patients with Fibromyalgia," *Journal of Rheumatology*, vol. 31, No. 6, pp. 1193-1199 (Jun. 2004).
Roche, F. et al., "Cardiac Interbeat Interval Increment for the Identification of Obstructive Sleep Apnea," *PACE*, vol. 25, No. 8, pp. 1192-1199 (Aug. 2002).
Roche, F. et al., "Predicting sleep apnoea syndrome from heart period: a time-frequency wavelet analysis," *European Respiratory Journal*, vol. 22, No. 6, pp. 937-942 (Dec. 2003).
Roche, F. et al., "Screening of Abstructive Sleep Apnea Syndrome by Heart Rate Variability Analysis," *Circulation*, vol. 100, No. 13, pp. 1411-1415 (Sep. 28, 1999).
Roehrs, T. et al., "Predictors of Objective Level of Daytime Sleepiness in Patients with Sleep-Related Breathing Disorders," *Chest*, vol. 95, No. 6, pp. 1202-1206 (Jun. 1989).
Sateia, M.J., "Neuropsychological impairment and quality of life in obstructive sleep apnea," *Clinics in Chest Medicine*, vol. 24, No. 2, pp. 249-259 (Jun. 2003).
Schaefer, K.E. et al., "Effect of 18-h watch schedules on circadian cycles of physiological functions during submarine patrols," *Undersea Biomedical Research*, vol. 6, Supplement: Preventive Aspects of Submarine Medicine, pp. S81-S90 (1979).
Shamsuzzaman, A.S.M. et al., "Obstructive Sleep Apnea: Implications for Cardiac and Vascular Disease," *Journal of the American Medical Association*, vol. 290, No. 14, pp. 1906-1914 (Oct. 8, 2002).
Shiomi, T. et al., "Augmented Very Low Frequency Component of Heart Rate Variability During Obstructive Sleep Apnea," vol. 19, No. 5, pp. 370-377 (Jun. 1996).
Shouldice, R.B. et al., "Detection of Obstructive Sleep Apnea in Pediatric Subjects using Surface Lead Electrocardiogram Features," *Sleep*, vol. 27, No. 4, pp. 784-792 (Jun. 15, 2004).
Stein, P.K. et al., "A Simple Method to Identify Sleep Apnea Using Holter Recordings," *Journal of Cardiovascular Electrophysiology*, vol. 14, No. 5, pp. 467-473 (May 2003).
Stoilova, I.M. et al., "How Human Sleep in Space—Investigations During Space Flights," *Advances in Space Research*, vol. 31, No. 6, pp. 1611-1615 (2003).
Stradling, J.R. and Davies, R.J.O., "Sleep 1: Obstructive sleep apnoea/hypopnoea syndrome: definitions, epidemiology, and natural history," *Thorax*, vol. 59, No. 1, pp. 73-78 (Jan. 2004).
Tateishi, O. et al., "Apnea-Related Heart Rate Variability in Congestive Heart Failure Patients," *Clinical and Experimental Hypertension*, vol. 25, No. 3, pp. 183-189 (2003).
Terzano, M.G. And Parrino, L., "Origin and Significance of the Cyclic Alternating Pattern (CAP)," *Sleep Medicine Reviews*, vol. 4, No. 1, pp. 101-123 (Feb. 2000).
Terzano, M.G. et al., "Atlas, rules, and recording techniques for the scoring of cyclic alternating pattern (CAP) in human sleep," *Sleep Medicine*, vol. 2, No. 6, pp. 537-553 (Nov. 2001).
Terzano, M.G. et al., "Atlas, rules, and recording techniques for the scoring of cyclic alternating pattern (CAP) in human sleep," *Sleep Medicine*, vol. 3, pp. 187-199 (2002).
Terzano, M.G. et al., "CAP variables and arousals as sleep electroencephalogram markers for primary insomnia," *Clinical Neurophysiology*, vol. 114, No. 9, pp. 1715-1723 (2003).
Terzano, M.G. et al., "The Cyclic Alternating Pattern as a Physiologic Component of Normal NREM Sleep," *Sleep*, vol. 8, No. 2, pp. 137-145 (Jun. 1985).
Terzano, M.G. et al., "Modifications of sleep structure induced by increasing levels of acoustic perturbation in normal subjects," *Electroencephalography & Clinical Neurophysiology*, vol. 76, No. 1, pp. 29-38 (Jul. 1990).

Terzano, M.G. et al., "Polysomnographic Analysis of Arousal Responses in Obstructive Sleep Apnea Syndrome by Means of the Cyclic Alternating Pattern," *Journal of Clinical Neurophysiology*, vol. 13, No. 2, pp. 145-155 (Mar. 1996).

"The Report of an American Academy of Sleep Medicine Task Force: Sleep-Related Breathing Disorders in Adults: Recommendations for Syndrome Definition and Measurement Techniques in Clinical Research," *Sleep*, vol. 22, No. 5, pp. 667-689 (1999).

Thomas, R.J., "Cyclic alternating pattern and positive airway pressure titration," *Sleep Medicine*, vol. 3, pp. 315-322 (2002).

Thomas, R.J., "Flow-limitation and sleep: exploring the interface of a complex and dynamic system," *Sleep Medicine*, vol. 2, pp. 375-377 (2002).

Tsai, W.H. et al.," A Comparison of Apnea-Hypopnea Indices Derived from Different Definitions of Hypopnea," *American Journal of Respiratory and Critical Care Medicine*, vol. 159, No. 1, pp. 43-48 (Jan. 1999).

Viola, A.U. et at, "Sleep as a Tool for Evaluating Autonomic Drive to the Heart in Cardiac Transplant Patients," *Sleep*, vol. 27, No. 4, pp. 641-647 (Jun. 15, 2004).

Whitney, C.W. et al., "Reliability of Scoring Respiratory Disturbance Indices and Sleep Staging," *Sleep*, vol. 21, No. 7, pp. 749-757 (Nov. 1, 1998).

Wolk, R. and Somers, V.K., "Cardiovascular consequences of obstructive sleep apnea," *Clinics in Chest Medicine*, vol. 24, No. 2, pp. 195-205 (Jun. 2003).

Yang, C.C.H. et al., "Relationship between electroencephalogram slow-wave magnitude and heart rate variability during sleep in rats," *Neuroscience Letters*, vol. 336, No. 1, pp. 21-24 (2003).

Younes, M., "Contributions of Upper Airway Mechanics and Control Mechanisms to Severity of Obstructive Apnea," *American Journal of Respiratory and Critical Care Medicine*, vol. 168, No. 6, Part 1, pp. 645-658 (Sep. 15, 2003).

Young, T. et al., "Epidemiology of Obstructive Sleep Apnea: A Population Health Perspective," *American Journal of Respiratory and Critical Care Medicine*, vol. 165, No. 9, pp. 1217-1239 (May 1, 2002).

Lipsitz, L.A. et al., "Heart Rate and Respiratory Rhythm Dynamics On Ascent to High Altitude," *British Heart Journal* 74(4):390-396 (Oct. 1995), http://heart.binjjournals.com/cgi/content/abstract/74/4/390 (printed on Apr. 25, 2005, 2 pages).

Moody, G.B. et al., "Clinical Validation Of the ECG-Derived Respiration (EDR) Technique," Computers in Cardiology 1986, vol. 13, IEEE Computer Society Press, Washington, D.C., pp. 507-510, http://www.physionet.org/physiotools/edr/cic86/edr86.html (printed Apr. 12, 2005, 6 pages).

Moody, G., B., "Derive A Respiration Signal From An ECG," Feb. 13, 1986 (last revised: Jan. 21, 2004), http://www.physionet.org/physiotools/edr/edr.c (printed Apr. 12, 2005, 6 pages).

Moody, G.B. et al., "Derivation Of Respiratory Signals From Multi-Lead ECGs," Computers in Cardiology 1985, vol. 12, IEEE Computer Society Press, Washington, D.C., pp. 113-116, http://www.physionet.org/physiotools/edr/cic85/edr85.html, (printed Apr. 12, 2005, 8 pages).

Moody, G.B., "ECG-Derived Respiration," http://www.physionet.org/physiotools/edr/, (printed Apr. 12, 2005, 2 pages).

\* cited by examiner

ASSESSMENT OF SLEEP QUALITY AND SLEEP DISORDERED BREATHING BASED ON CARDIOPULMONARY COUPLING

CROSS-REFERENCE TO RELATED APPLICATIONS

This application is a continuation-in-part of U.S. application Ser. No. 10/846,945, filed May 17, 2004, by Mietus et al., entitled "Assessment of Sleep Quality and Sleep Disordered Breathing Based on Cardiopulmonary Coupling," incorporated herein by reference in its entirety.

STATEMENT REGARDING FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The present invention relates generally to analyzing physiologic data, and more specifically, to non-invasively assessing sleep pathology and physiology from coherence and/or cross-power measurements.

2. Related Art

At least five percent of the general population suffers from medically significant sleep disorders, the most common being sleep-disordered breathing (also known as sleep apnea). As a major public health concern, sleep disorders contribute to excessive daytime sleepiness and the associated risks of driving accidents, hypertension, heart attacks, strokes, depression, and attention deficit disorders. The prevalence of sleep disorders is much higher (exceeding thirty percent) in select populations such as, individuals having obesity, congestive heart failure, diabetes, and renal failure.

Conventional diagnostic systems for detecting sleep disorders typically involve complex multiple channel recordings in a sleep laboratory and labor intensive scoring, which collectively lead to substantial expense and patient discomfort. An example of a conventional sleep diagnostic system is a full polysomnograph. Polysomnography is the gold standard for detection and quantification of sleep-disordered breathing, and includes sleep staging, scoring of respiratory abnormality (e.g., apneas, hypopneas, flow-limitation, periodic breathing, and desaturation episodes), and limb movements. Typical markers of sleep disorder severity are the sleep fragmentation index, the apnea-hypopnea index, the respiratory disturbance index, an arousal frequency or index, and the oxygen desaturation index.

One of the many limitations of conventional sleep diagnostic systems is the dependence on tedious manual scoring of "events" based on physiologically arbitrary criteria. Only a moderate correlation can be found between these events and cognitive and cardiovascular outcomes. As such, conventional systems leave a significant amount of unexplained variance in effect, and fail to adequately describe the physiologic impact of sleep disorders. Therefore, a quantitative measure that evaluates the impact of sleep disorders on sleep physiology could be useful in clarifying some of the unexplained variance. A continuous biomarker of physiological state may be particularly useful to follow treatment effects. A continuous biomarker may also be useful to discriminate those in whom the seemingly subtle sleep disorder disease is physiologically disruptive. Such physiologically disruptive settings include primary snoring, which, in adults is associated with excessive sleepiness, and in children is associated with inattentive and/or hyperactive behaviors.

Presently, rapid and accurate throughput of sleep diagnostics does not exist, despite the development of limited forms of sleep testing that include various combinations of airflow, respiratory effort, electrocardiogram (ECG), and oximetry. This is especially problematic in conditions such as congestive heart failure and chronic renal failure, where severe and complex forms of sleep apnea may adversely affect both mortality and morbidity. Since conventional sleep studies are so expensive, information on sleep effects are typically limited in the pre-approval assessments of drugs used in neurological and psychiatric practice.

A complementary dimension of assessment in sleep-disordered breathing is the differentiation of obstructive from non-obstructive disease. While the extreme forms of non-obstructive disease are readily identified on standard sleep studies (e.g., central sleep apnea syndrome and Cheyne-Stokes respiration), all degrees of admixture of physiological abnormalities can be seen in clinical practice. Moreover, the physiology can change within the same night based on body position, time of night effects, and sleep stage effects. A method to track physiological switches from obstructive to central pathophysiology that occur spontaneously or are induced by treatment has practical utility, as treatments for these two conditions are different.

Obstructive disease responds well to positive airway pressure, while non-obstructive disease responds poorly to such therapy and may in fact be exaggerated by air pressure. Individuals with certain disease states are at high risk for mixed physiology disorders, including but not restricted to congestive heart failure, chronic renal failure, and post-stroke sleep apnea syndromes. A simple method to assess disease pathophysiology at the diagnostic level can allow modifications of the clinical treatment approach such that therapies that improve central dysfunction may be initiated earlier in the process.

As obstructive disease responds to mechanical therapies (that support the airway) and non-obstructive disease to control-specific approaches (such as, but not limited to, inhalation of oxygen or carbon dioxide), identification of these two types of physiological abnormalities may also allow prognostication of treatment outcomes (prediction of success or failure of therapy).

Therefore, a need exists to develop a technology that can provide a simple, inexpensive, repeatable measure of the presence and impact of a variety of sleep disruptive stimuli (such as noise, pain, drugs, mood disorders, disordered breathing) on sleep state physiology and stability.

SUMMARY OF THE INVENTION

The present invention provides a method, system and computer program product for performing a quantitative analysis of cardiopulmonary coupling between two physiological signals to detect and evaluate sleep physiology and pathology. According to embodiments of the present invention, an R-R interval series is combined with a corresponding respiration signal to determine the coherent cross-power of these two signals. The coherent cross-power provides a measure of cardiopulmonary coupling.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable one skilled in the pertinent art(s) to make and use the invention. In the drawings, generally, like reference numbers indicate identical or functionally or structurally similar elements. Additionally, generally, the leftmost digit(s) of a reference number identifies the drawing in which the reference number first appears.

DETAILED DESCRIPTION OF THE INVENTION

Figure 1:
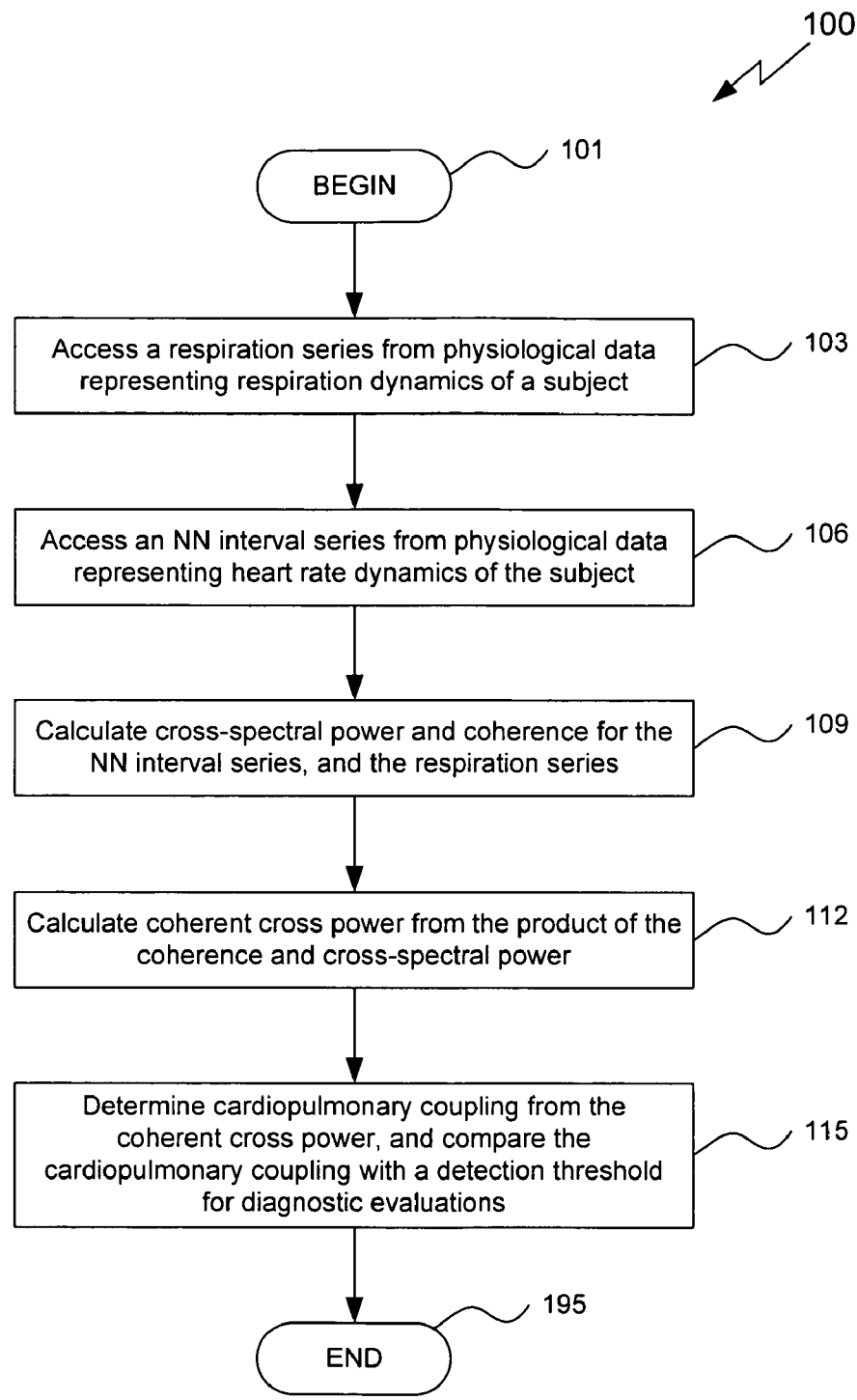
FIG. 1 illustrates an operational flow for detecting cardiopulmonary coupling according to an embodiment of the present invention.

According to embodiments of the present invention, a method, system, and computer program product is provided to perform a quantitative analysis of cardiopulmonary coupling between two physiological signals to detect and evaluate sleep physiology.

This specification discloses one or more embodiments that incorporate the features of this invention. The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Sleep is a complex state characterized by cycling stages (i.e., rapid eye movement (REM) sleep and non-REM sleep) and a sequence of progressive and regressive depths (i.e., stages I to IV in non-REM sleep). There is also a stability dimension that has been recognized, but not generally applied in clinical practice, based on the concept of cyclic alternating pattern (CAP) in non-REM sleep. CAP-type non-REM sleep is unstable, whereas, non-CAP non-REM sleep is a restful, non-aroused state with a stabilizing influence.

The distribution of stages and states of sleep can be altered by numerous sleep disrupting extrinsic factors (e.g., noise, heat, cold, vibration, barotraumas, motion, gravitational stress, etc.) and intrinsic factors (e.g., disordered breathing, pain, seizures, restless legs, periodic limb and related movements, etc.). More importantly, these factors all induce CAP, a state characterized by periodic behavior in multiple measures (such as, brain electrical activity, heart rate, respiration, and blood pressure). In the non-CAP state, physiological stability exists.

Sleep disordered breathing (SDB) is associated with the emergence of relatively low frequency (i.e., 0.01 to 0.1 Hertz (Hz)) periodic behavior in multiple physiologic systems, such as respiration, heart rate, and electroencephalographic (EEG) activity. These pathological oscillations represent periods of physiologically unstable sleep behavior and low frequency coupling of respiration-driven ECG variability. In this state, the EEG pattern typically displays CAP attributes.

In contrast, periods of stable breathing are associated with the non-CAP EEG pattern and high frequency (i.e., 0.1 to 0.4 Hz) coupling between respiration and beat-to-beat heart rate variability (e.g., respiratory sinus arrhythmia). In patients with SDB, spontaneous and relatively abrupt transitions tend to occur between these two states.

As described in greater detail below, the present invention provides techniques and/or methodologies for quantifying cardiopulmonary coupling, which shows a strong correlation with CAP and non-CAP states. Accordingly, the present invention provides a biomarker of sleep physiology and pathology, such as the percentage of sleep spent in periods of unstable sleep behavior.

Referring to FIG. 1, flowchart 100 represents the general operational flow of an embodiment of the present invention. More specifically, flowchart 100 shows an example of a control flow for detecting cardiopulmonary coupling from a subject (such as, a patient, test/laboratory subject, or the like).

The control flow of flowchart 100 begins at step 101 and passes immediately to step 103. At step 103, a set of interval respiration data (referred to herein as a "respiration series") is accessed from a physiological signal. The physiological signal can be an electrocardiogram (ECG or EKG), from which a surrogate respiratory signal is obtained, as described in greater detail below. However, the physiological signal can be any type of signal representing respiration dynamics in the subject. As such, the respiration data series can be derived from, for example, a nasal thermistor, forced oscillation, acoustic reflectance techniques, nasal-cannula pressure transducer system, impedance/inductance/piezo chest and/or abdominal effort band, or the like.

At step 106, a set of interval heart rate data (referred to herein as a "R-R interval series") is accessed from a physiological signal. In an embodiment, the heart rate physiological signal is the same physiological signal that provides the respiration interval signal that is described above at step 103. In another embodiment, the heart rate physiological signal is distinct from the physiological signal that provides the respiration signal. Moreover, the heart rate physiological signal can be the same type of signal (e.g., both being ECG) or a different type of signal (e.g., ECG for the heart rate interval series, and nasal-cannula pressure-transducer nasal thermistor flow for the respiration series) as the physiological signal that provides the respiration signal.

Accordingly, the heart rate physiological signal is any type of signal that enables the derivation of a series of heart rate interval data (i.e., R-R intervals or R-R equivalent intervals). Thus, the heart rate physiological signal can be any type of signal representing heart rate dynamics in the subject. Such signal can be derived from, for example, ECG, blood pressure, pulse Doppler flow (e.g., sensed via ultrasound recording), ECG signal from another electrical signal (e.g., EEG), or the like.

Regardless of their source(s), the heart rate interval series and respiration series must be temporally aligned to determine the cardiopulmonary coupling. In an embodiment, the normal sinus (N) beats are selected from the heart rate interval series to produce a series of normal-to-normal (NN) heart rate data (referred to herein as an "NN interval series"). The respiration series would therefore be temporally aligned with the NN interval series.

At step 109, cross-spectral power and coherence is calculated using both the heart rate interval series (or NN interval series) and respiration series. At step 112, the product of the coherence and cross-spectral power calculations are taken to derive a set of coherent cross-power calculations. At step 115, the coherent cross-power calculations are used to determine the cardiopulmonary coupling. As described in greater detail below, the cardiopulmonary coupling can be compared with one or more detection thresholds for diagnostic evaluations, such as SDB screening or the like. Afterwards, the control flow ends as indicated at step 195. As such, the present invention provides for a fully automated quantitative analysis of cardiopulmonary coupling that can be used, for example, to screen for SDB, assess physiological impacts of SDB, and/or monitor the therapeutic effects of different approaches to treating SDB, or the like.

Figure 2:
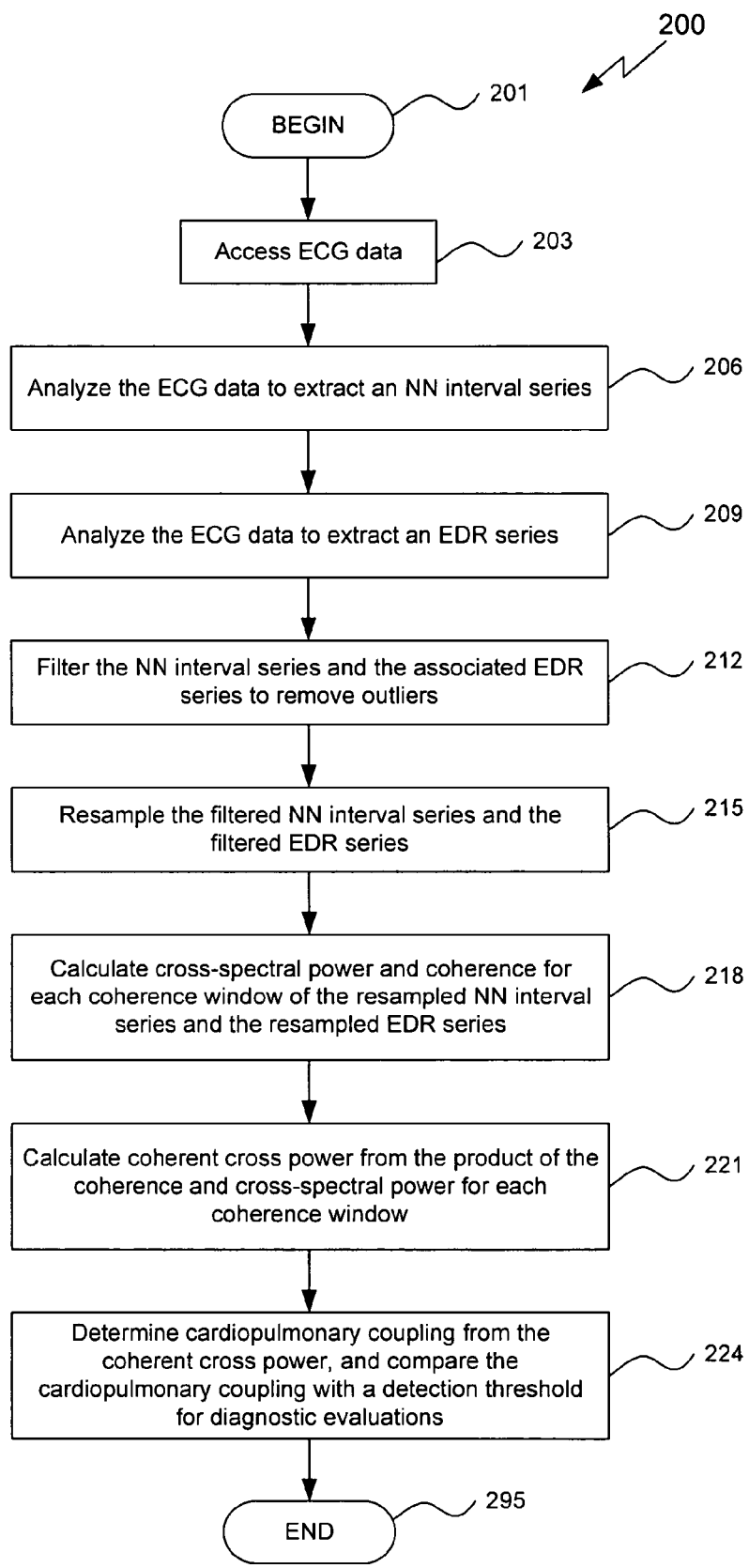
FIG. 2 illustrates an operational flow for using ECG-derived respiration to quantify cardiopulmonary coupling according to an embodiment of the present invention.

Referring to FIG. 2, flowchart 200 represents the general operational flow of another embodiment of the present invention. More specifically, flowchart 200 shows an example of a control flow for quantifying cardiopulmonary coupling by using ECG-derived respiration (EDR) to integrate R-R variability and fluctuations in cardiac electrical axis associated with respiration.

The control flow of flowchart 200 begins at step 201 and passes immediately to step 203. At step 203, an ECG signal or set of ECG data is accessed. In an embodiment, surface ECG data is retrieved from a storage medium. In another embodiment, surface ECG data is obtained directly from an ECG monitoring device. For example, ECG data can be obtained, in real time or otherwise, from a Holter monitor or recording from an ECG monitor such as those available from GE Marquette Medical Systems (Milwaukee, Wis.) or other sources.

A single or two lead ECG signal is obtained directly from an ECG monitoring device. If using one lead, the skin sensor or electrode should be placed at or near the V2 chest position. If using two leads, it is preferable to position the electrodes relatively orthogonal to each other. However, other chest positions can be used to obtain the single or two lead ECG data.

At step 206, the ECG data is analyzed to detect and classify heart beats (i.e., R-R intervals), from the ECG data, as being normal (N) or ectopic. An automated beat detection and annotation routine or function is used to process digitized ECG data from a Holter recording. The routine detects and classifies (i.e., labels) the heart beats from the digitized data. The output is a time series of annotated heart beats (i.e., "R-R interval series"). This series is then processed to retain only normal-to-normal sinus beats (i.e., "NN interval series").

At step 209, the ECG data is analyzed to extract a time series of QRS amplitude variations (i.e., "EDR series") that are associated with the NN interval series. The amplitude variations in the QRS complex (from the normal beats) are due to shifts in the cardiac electrical axis relative to the electrodes during respiration. From these amplitude variations, a surrogate respiratory signal (i.e., EDR) is derived. The same function or routine used to extract the NN interval series is also used to measure the QRS amplitudes for the heart beats, and produce a continuous EDR signal.

At step 212, the NN interval series and the associated EDR series are analyzed to detect and/or remove any outliers due to false detections or missed detections. For example, during step 206, the automated beat detection function may generate a false detection or fail to detect a normal data point for the NN interval series (and, hence the associated EDR series). A sliding window average filter is used to remove the outliers, as described with reference to FIG. 3 in greater detail below.

At step 215, the filtered NN interval series and the filtered EDR series are resampled. The resampling rate depends on the subject class, and is selected to optimize the data series for the spectra calculations described in the following steps. For example, for human subjects, both series are resampled at two Hz. For premature or neonatal subjects (who are approximately less than one year of age), a four Hz resampling rate is used because neonatal infants typically have a heart rate that is approximately twice the rate of an adult. For nonhuman subjects (such as, laboratory mice), a twenty Hz resampling rate is used.

At step 218, cross-spectral power and coherence are calculated for overlapping windows of data selected from both the resampled NN interval series and the resampled EDR series. A Fast Fourier Transform (FFT) is used to compute the cross-spectral power and coherence calculations for the two signals. As described in greater detail below with reference to FIG. 4, a plurality of overlapping windows is used to perform the FFT computations.

At step 221, a data series of "coherent cross-power" are calculated from the product of the coherence and cross-spectral power calculations from step 218. For each window, the product of the coherence and cross-spectral power is used to calculate the coherent cross-power for each window of data.

If a coherent cross-power calculation falls within the range of 0 to 0.01 Hz, it is considered to be within the very low frequency (VLF) band. If the coherent cross-power falls within the range of 0.01 to 0.1 Hz, it is considered to be within the low frequency (LF) band. If the coherent cross-power falls within the range of 0.1 to 0.4 Hz, it is considered to be within the high frequency (HF) band. When making the VLF, LF, and HF determinations, one or more frequency bins in each band are used to make the calculations. The two bins having the greatest power are used.

At step 224, "cardiopulmonary coupling" is determined from the coherent cross-power. The cardiopulmonary coupling can be compared with a detection threshold for a variety of diagnostic applications. For example, the cardiopulmonary coupling can be compared with a predefined detection threshold to detect or evaluate sleep qualities, such as CAP activity, non-CAP activity, wake and/or REM activity, or the like.

For CAP activity, the coherent cross-power is used to calculate a ratio of coherent cross-power in the LF band to that in HF. An excess of coherent cross-power in the low frequency band is associated with periodic behaviors in the EEG (i.e., CAP) and periodic patterns of breathing. The detection thresholds may be 0.2 for the minimum LF power, and 2.0 for the minimum LF/HF ratio.

For non-CAP, the coherent cross-power is used to calculate a ratio of coherent cross-power in the LF band to that in HF. An excess of coherent cross-power in the high frequency band is associated with physiologic respiratory sinus non-CAP arrhythmia, stable non-periodic breathing patterns and non-CAP EEG. The detection thresholds may be 0.02 for the minimum HF power, and 1.5 for the maximum LF/HF ratio.

For wake and/or REM activity, the ratio of coherent cross-power in the VLF band to combined power in LF and HF allows detection of wake and/or REM. An excess of coherent cross-power in the VLF band tends to be associated with wake and/or REM. The detection thresholds may be 0.05 for the minimum VLF power and 0.2 for the maximum VLF-to-(LF+HF) ratio. In those with significant sleep-disordered breathing, REM sleep usually has coherent cross-power characteristics very similar and often indistinguishable from CAP physiology.

Upon completion of the cardiopulmonary coupling quantification and analyses, the control flow ends as indicated at step 295.

Figure 3:
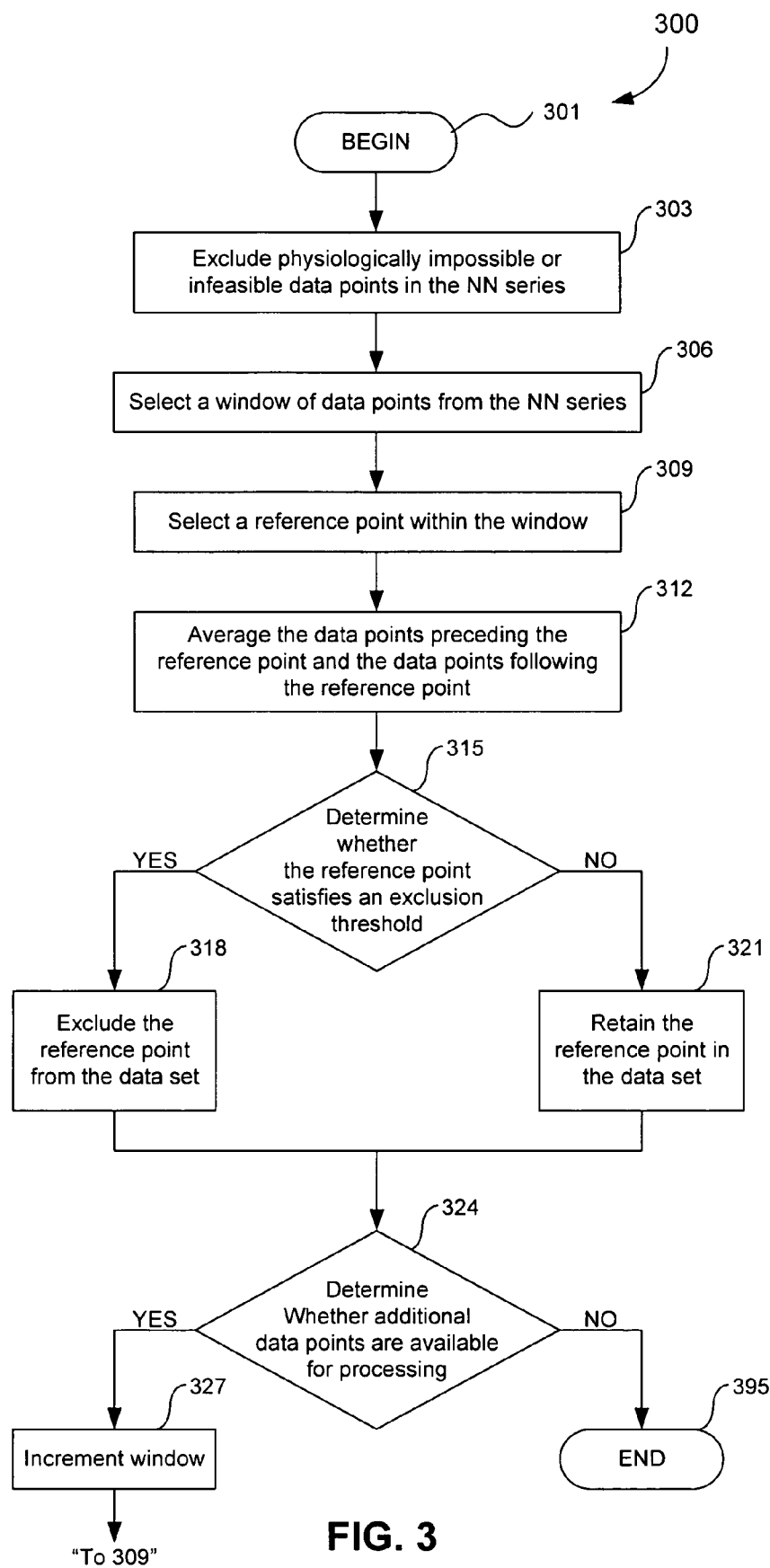
FIG. 3 illustrates an operational flow for removing outliers from a data interval series according to an embodiment of the present invention.

As described above with reference to step 212, the NN interval series and their associated EDR series are analyzed to detect and/or remove outliers due to false detections or missed detections. Referring to FIG. 3, flowchart 300 represents the general operational flow of an embodiment of the present invention for removing outliers from a data series. More specifically, flowchart 300 shows an example of a control flow for using a sliding window average to filter outliers.

The control flow of flowchart 300 begins at step 301 and passes immediately to step 303. At step 303, all data points in the NN interval series that are determined to be physiologically impossible or infeasible are excluded a priori. The a priori exclusion threshold differs according to the subject class. The a priori exclusion threshold may be an NN interval less than 0.4 seconds or an NN interval greater than 2.0 seconds.

At step 306, the window size is set to begin the averaging. The window size may be set for forty-one data points. Next, a first window (i.e., a first set of forty-one data points) is selected from the NN series.

At step 309, a reference point is selected from within the window. For example, the middle (or twenty-first) data point can be selected as the reference point.

At step 312, the twenty points preceding the reference point and the twenty points following the reference point are averaged. At step 315, it is determined whether the reference point equals or exceeds a predefined threshold based on the average value calculated at step 312. The reference point exclusion threshold may be set at twenty percent.

At step 318, the reference point is excluded from the data series if it satisfies the reference point exclusion threshold. For example, if the reference point exclusion threshold is set at twenty percent and the reference point deviates twenty percent or more from the averaged value, the reference point is excluded.

At step 321, the reference point remains in the data series if it does not satisfy the reference point exclusion threshold. For example, if the reference point exclusion threshold is set at twenty percent and the reference point deviates less that twenty percent of the averaged value, the reference point remains in the data set.

At step 324, the data series is checked to determine whether additional data is available for processing. If additional data is available, at step 327, the window is moved up one data point and the control flow returns to step 309 to repeat the search for outliers. Otherwise, the control flow ends as indicated at step 395.

The above parameters (i.e., a priori exclusion threshold, window size, reference point exclusion threshold) are provided by way of example and can be adjusted to optimize the quantification of cardiopulmonary coupling as desired by the operator.

Figure 4:
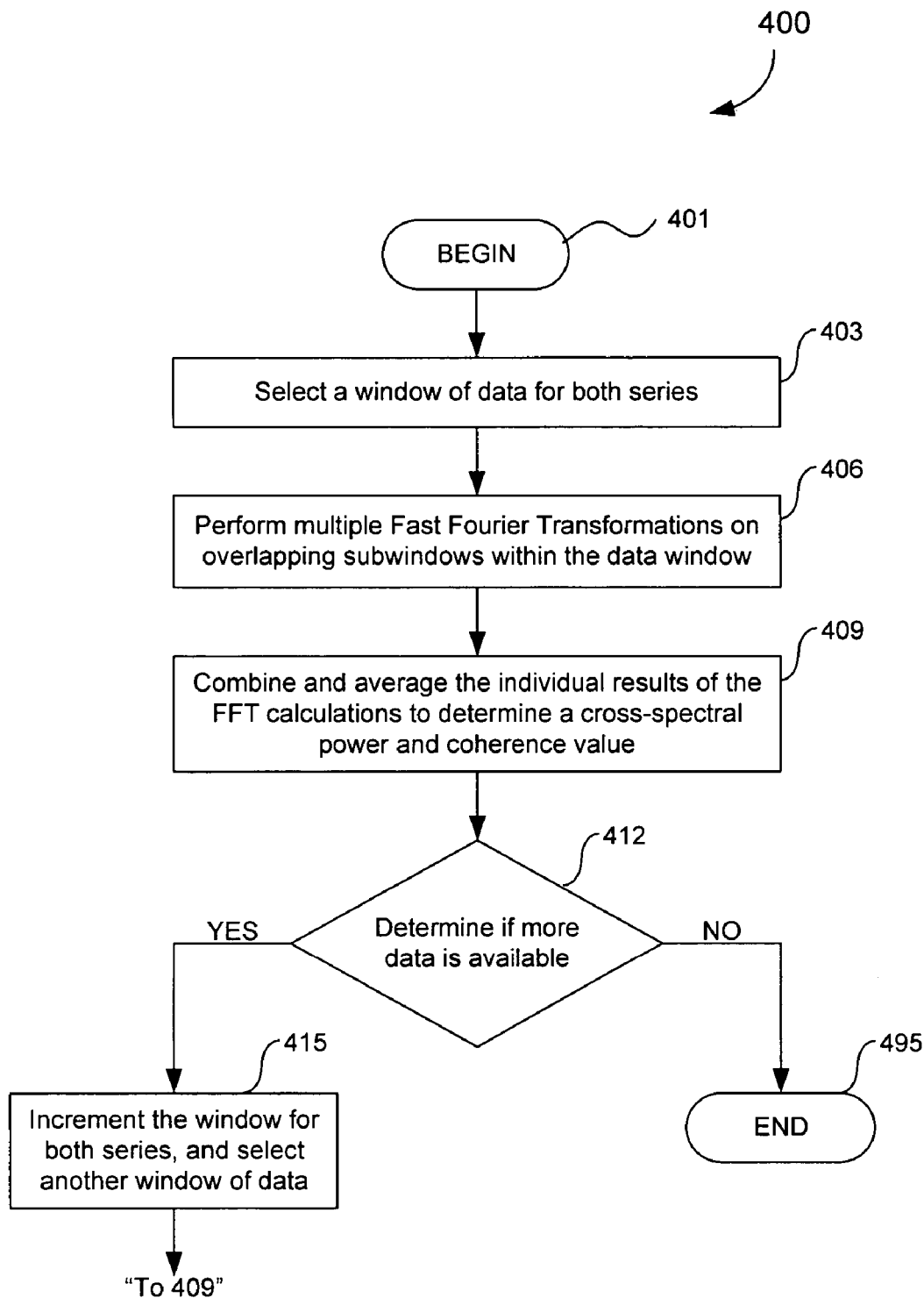
FIG. 4 illustrates an operational flow for calculating cross-spectral power and coherence according to an embodiment of the present invention.

As described above with reference to step 218, cross-spectral power and coherence are calculated for overlapping windows of data selected from both the NN interval series and their associated EDR series. The cross-spectral power and coherence of these two signals may be calculated over a 1,024 sample (e.g., approximately 8.5 minute) window using FFT applied to three overlapping 512 sample sub-windows within the 1,024 coherence window. Referring to FIG. 4, flowchart 400 represents the general operational flow of an embodiment of the present invention for calculating cross-spectral power and coherence. More specifically, flowchart 400 shows an example of a control flow for using FFT to calculate cross-spectral power and coherence of two data series.

The control flow of flowchart 400 begins at step 401 and passes immediately to step 403. At step 403, a window of data is selected.

At step 406, FFTs are performed within the selected window. Three FFTs may be performed within the selected window. A first FFT is performed at the beginning, a second transform at the middle, and a final transform at the end of the selected window. For each FFT, the size of the frequency bin is 512 data points. The intra-window increments are 256 points for the first, second and third FFT. Thus, the sub-windows overlap by fifty percent.

At step 409, the individual results of the FFT calculations are combined and averaged to determine a cross-spectral power and coherence value. In other words, for each 1,024 window, the three FFT calculations are combined and averaged to determine the cross-spectral power and coherence for a window of data.

At step 412, it is determined whether additional data are available for further FFT calculations. If additional data are available, at step 415, the next window of data is selected and the control flow returns to step 406 to apply FFT to three overlapping 512 sample sub-windows within the selected 1,024 coherence window. In other words, the previous 1,024 window (selected at step 403) is advanced by 256 samples (e.g., approximately 2.1 minutes) and three FFT calculations are performed.

Upon completion of the calculations for the entire NN and EDR data series, the control flow ends as indicated at step 495.

As discussed above, cardiopulmonary coupling can also be used to detect or evaluate SDB and its impact on sleep (e.g., the proportion of sleep time spent in CAP). For SDB, the coherent cross-power is used to calculate a ratio of coherent cross-power in the LF band to that in HF. An excess of coherent cross-power in the LF band is associated with CAP, periodic respiration, and EEG CAP. The detection thresholds may be 0.2 for the minimum LF power, and 50 for the minimum LF/HF ratio.

Figure 6:
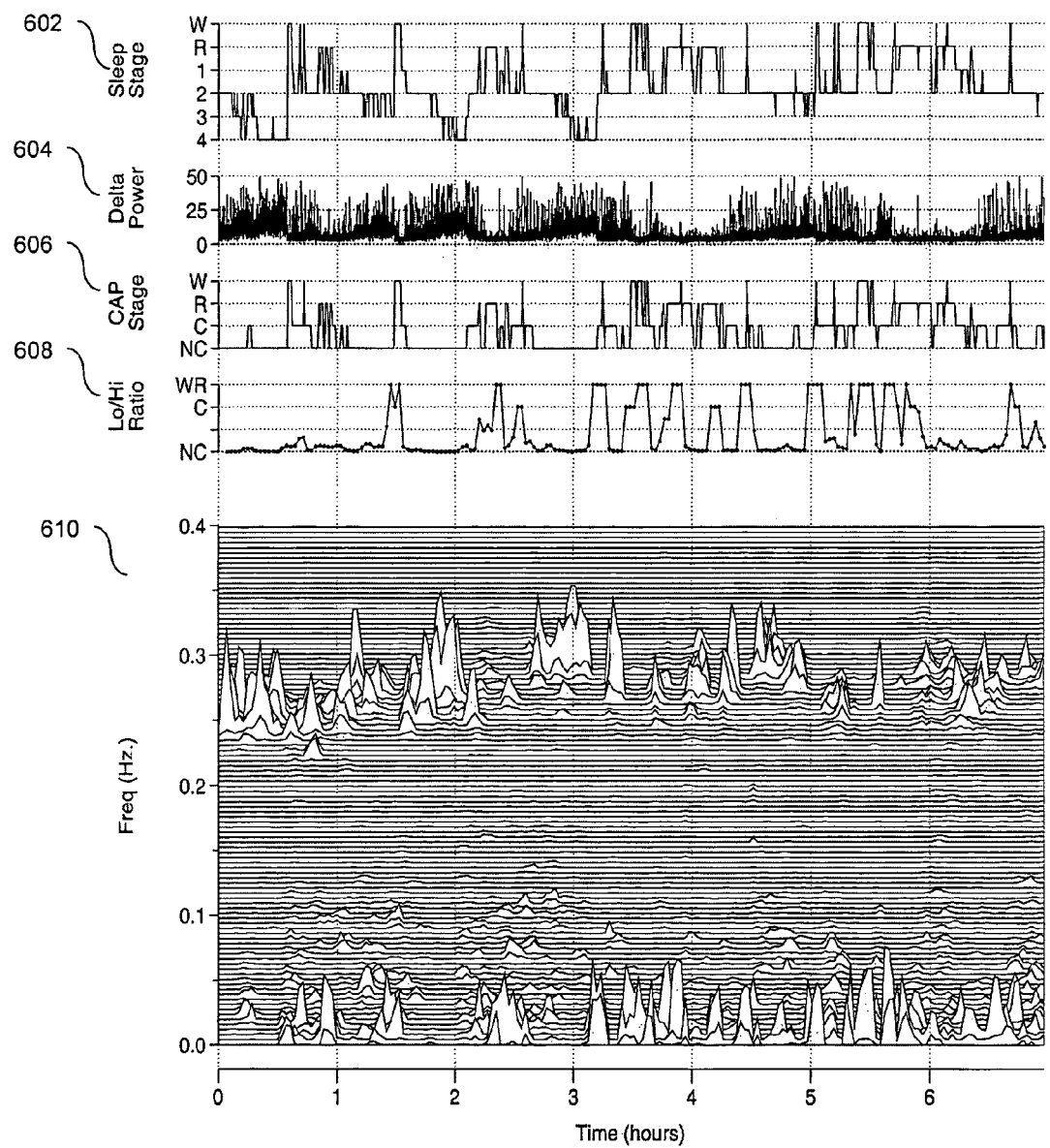
FIG. 6 illustrates a cardiopulmonary coupling analysis of a 22-year-old healthy female according to an embodiment of the present invention.

FIG. 6 illustrates a cardiopulmonary coupling analysis of a 22-year-old healthy adult female, according to an embodiment of the present invention. Specifically, FIG. 6 includes five panels 602-610 that analyze the sleep stages, delta power, CAP stages, ratio of low-to-high frequency coherent cross-power, and cardiopulmonary coupling spectrogram, respectively, for the 22-year-old subject. The abscissa for panels 602-610 represents time demarcated in hours. Along the ordinate axis of panels 602, 606, and 608, the notation "W" represents time spent in a wake stage, "R" represents time spent in REM sleep, "C" represents time spent in a CAP stage, and "NC" represents time spent in a non-CAP stage. The body position for the subject was supine throughout the study illustrated in FIG. 6.

Panel 610 shows a cardiopulmonary coupling spectrogram across seven hours of sleep, where the magnitude of the coherent cross-power at each frequency is indicated by the height of a peak. The sleep spectrogram reveals spontaneous switching between high-frequency and low-frequency coupled states represented by the two distinct bands of spectrographic peaks.

Using appropriate thresholds (as described above) for the power ratios, sleep demonstrating non-CAP, CAP, and wake/REM states can be identified from the cardiopulmonary coupling spectrogram (panel 610). Panel 602 shows conventional sleep stages scored in 30-second epochs. The sleep stages are scored in 30-second epochs and the ECG-derived coherent cross-power is calculated every 2.1 minutes. A 30-second linear interpolation is used to calculate spectral power corresponding to each scored epoch.

CAP scoring (for distinguishing among non-CAP, CAP, and wake/REM states) can be explained with reference to panels 604-608. The CAP scoring in, for example, panel 606 is determined independently of polysomnogram scoring (e.g. panel 602). The standard epoch duration for scoring CAP is typically sixty seconds. To improve state detection, the scoring is modified to allow 30-second designations by viewing a polysomnogram screen in 30-second epochs and designating each epoch as CAP or non-CAP. If there is ambiguity or difficulty with a designation, the epoch duration can be changed to sixty seconds to make a state determination.

A CAP sequence includes at least two consecutive cycles, and each CAP cycle comprises two components: phase A and phase B. Phase A includes EEG transients, and phase B is defined as the interval of delta/theta activity that separates two successive A phases. The duration of each phase ranges from two to sixty seconds. Functionally, CAP is a state of sleep instability alternating between a higher arousal level (Phase A) and a lower level (Phase B). Subjects with severe sleep-disordered breathing have an increase in the proportion of sleep time spent in low-frequency coupling and CAP (e.g., greater than 80%, at the expense of non-CAP), with apneas, hypopneas, and flow-limitation typically occurring during the B phases.

Phase A characteristics includes intermittent alpha rhythm and sequences of vertex sharp waves in stage I sleep. Phase A is also characterized by having sequences of two or more K-complexes, with or without alpha and beta rhythms. Phase A includes delta bursts that show a difference in amplitude of at least one-third compared with background activity. Phase A also includes transient activation phases of microarousals in stage I and II or at the end of stage III and IV, characterized by an increase in EEG frequency with decreased amplitude, disappearance of sleep spindles and delta activity when occurring in slow wave sleep, transitory enhancement of muscle tone or appearance of electromyography activity, body movements, postural changes, and acceleration of heart rate.

There is a further separation of A phases based on the proportion of faster and slower morphologies. For instance, A1 CAP is dominated by synchronized EEG patterns, including alpha rhythm in stage I, sequences of K-complexes in stage II, and delta bursts in stage III and IV. A2 CAP has evidence of both synchronization and desynchronization, but the amount of EEG desynchrony does not exceed two thirds of the total A phase duration. Features of A2 CAP include K-complexes with alpha and beta activities, K-alpha, and microarousals with slow wave synchronization. A3 CAP shows predominantly EEG desynchronization (e.g., greater than two-thirds duration of phase A), and arousals and microarousals coupled with a powerful activation of muscle tone and cardiorespiratory parameters.

A1 CAP is rare, usually physiological, and especially seen during transitions into and out of delta sleep and briefly prior to a REM sleep period. A2 CAP and A3 CAP are often pathological and associated with sleep disruptive states.

Referring back to FIG. 6, panel 604 shows the second-by-second delta power from the C4-A1 EEG montage (μV2). Panel 606 shows EEG-based manual CAP scoring for the sleep states non-CAP, CAP, wake, and REM. The CAP scoring of panel 606 is graphed along with the classic sleep stages of panel 602 to allow a direct visual comparison. CAP detection (Panel 608) may be implemented by first detecting non-CAP by using power thresholds giving the maximal sensitivity and specificity for non-CAP epoch-by-epoch detection. Specifically, a given minimum high-frequency power and a low-to-high ratio below a set value is required. If an epoch is not detected as non-CAP, CAP detection criteria is applied by using thresholds giving maximal sensitivities and specificities for epoch-by-epoch detection. Here, there is a requirement for a given minimum low-frequency power and a low-to-high ratio above a set value. Finally, if an epoch is not detected as either non-CAP or CAP, wake/REM is detected by using thresholds giving maximal sensitivity and specificity for its epoch-by-epoch detection. For this detection, there is a requirement for a minimum very low-frequency power and a minimum ratio of very low to combined low and high-frequency power. On average, a small percentage of epochs (approximately 4%) may not be detectable as non-CAP, CAP or wake/REM, and may be classified as "other."

Panel 608 shows the ratio of low (0.01-0.1 Hz) to high (0.1-0.4 Hz) frequency coherent cross-power (Lo/Hi Ratio) used to detect the sleep state. For each of the three sleep states of non-CAP, CAP, and combined wake/REM, separate receiver-operator curves are calculated over a range of power ratio thresholds, and the thresholds giving the maximum combined sensitivities and specificities for that state were selected as optimal for the detection of that state. During the second half of the sleep period, there is the continued occurrence of cycles of increased delta power and high-frequency coupling that correlate with non-CAP sleep.

Figure 7:
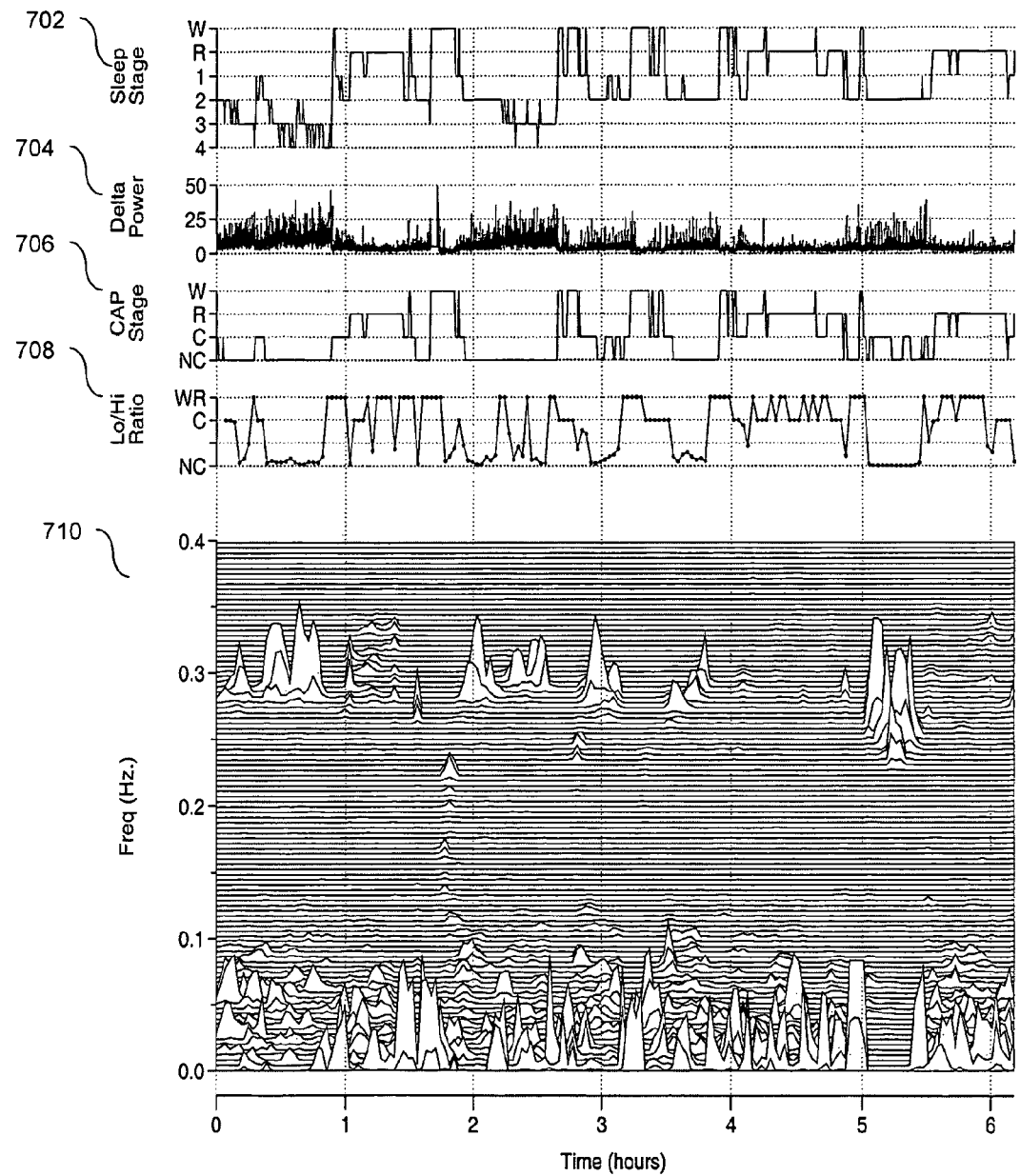
FIG. 7 illustrates a cardiopulmonary coupling analysis of a 56-year-old healthy female according to an embodiment of the present invention.

FIG. 7 illustrates a cardiopulmonary coupling analysis of a 56-year-old healthy female. Panels 702-710 are comparable to panels 602-610 of FIG. 6, with a sleep spectrogram depicted in panel 710. The body position for the subject was supine throughout the study illustrated in FIG. 7.

Panel 704 shows an expected age-related reduction in delta power and scored slow-wave sleep. Despite this decline relative to a younger individual, the cardiopulmonary coupling profile (as shown by panels 704-710) across the sleep period retains the same type of switching pattern between low and high-frequency coupled states that track with CAP and non-CAP, respectively.

Both subjects from FIG. 6 and FIG. 7 demonstrate spontaneous shifts between low-frequency and high-frequency coupling regimes that occur independent of body position, age, conventional sleep staging, and delta power, as shown in FIG. 6 and FIG. 7. These distinct states have characteristic and predictable EEG, respiratory, and heart rate variability signatures, and occur independently of standard sleep staging but correlate with CAP scoring.

Cardiopulmonary coupling can also be used to assess physiological impacts of the aforesaid sleep qualities, SDB, or the like. The cardiopulmonary coupling can also be used monitor the therapeutic effects of different approaches to treating the aforesaid sleep qualities, SDB, or the like. Hence, as described above, the present invention combines the use of mechanical and autonomic effects of, for example, SDB on ECG parameters.

Figure 8:
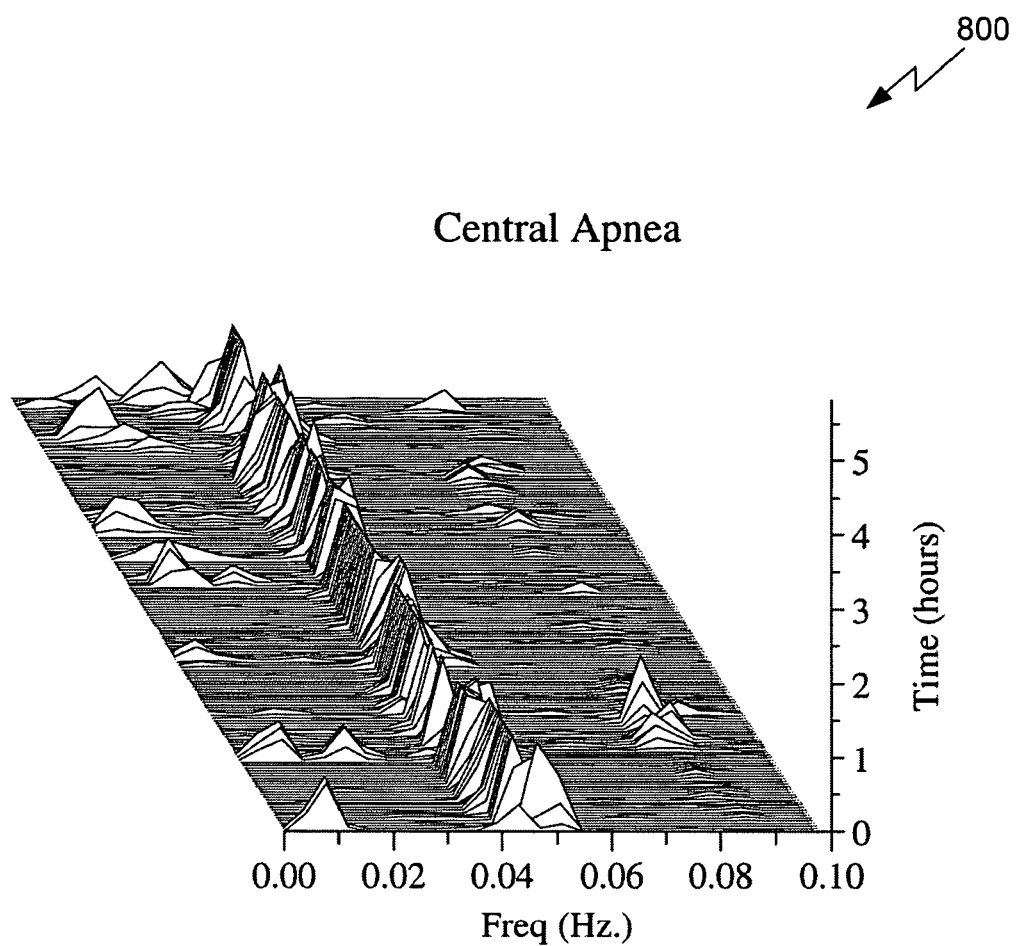
FIG. 8 illustrates a spectrogram of cardiopulmonary coupling for diagnosing central apnea according to an embodiment of the present invention.
Figure 9:
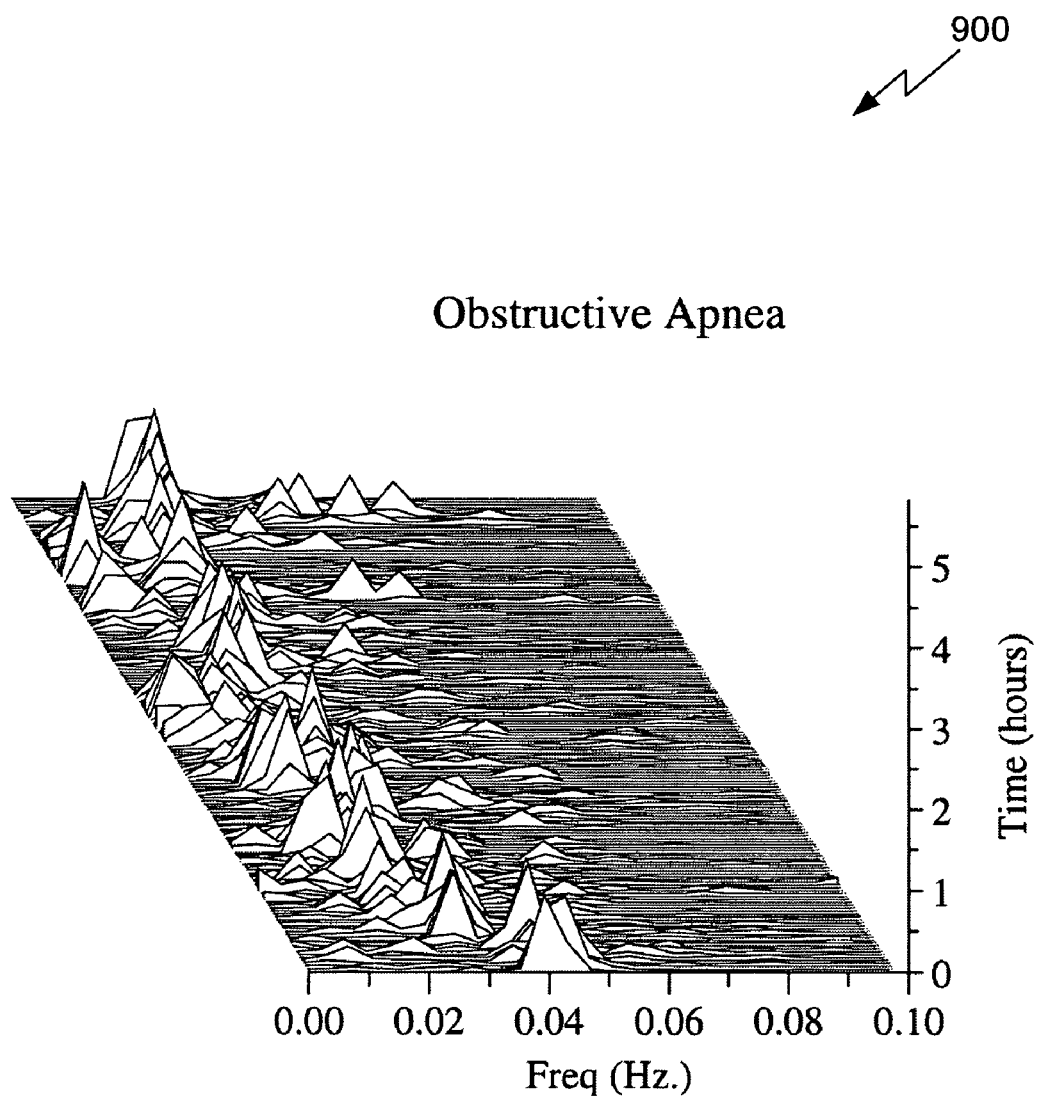
FIG. 9 illustrates a spectrogram of cardiopulmonary coupling for diagnosing obstructive apnea according to an embodiment of the present invention.

A complementary dimension of sleep physiology that can be assessed with cardiopulmonary coupling is the differentiation of predominantly obstructive from predominantly non-obstructive disease, and various admixtures of the same. This information is extracted from the spectral dispersion and number of spectral peaks obtained from low-frequency cardiopulmonary coupling. This can be explained with reference to FIG. 8 and FIG. 9, both of which illustrates a spectrogram of cardiopulmonary coupling. FIG. 8 illustrates a spectrogram 800 for diagnosing central apnea. FIG. 9 illustrates a spectrogram 900 for diagnosing obstructive apnea.

For an obstructive disease (as shown in FIG. 9), the mechanics of the upper airway do not allow a precise timing of respiratory events, resulting in multiple spectral peaks, broad coupling spectra, or both. For a non-obstructive disease (as shown in FIG. 8), the oscillation of respiratory control results in a single dominant frequency, usually with a narrow spectral dispersion. Treatments that primarily target one pathophysiology in a patient with mixed disease may be expected to result in a conversion to predominance of the other pattern, and such dynamics can be captured by cardiopulmonary coupling assessments.

Figure 10:
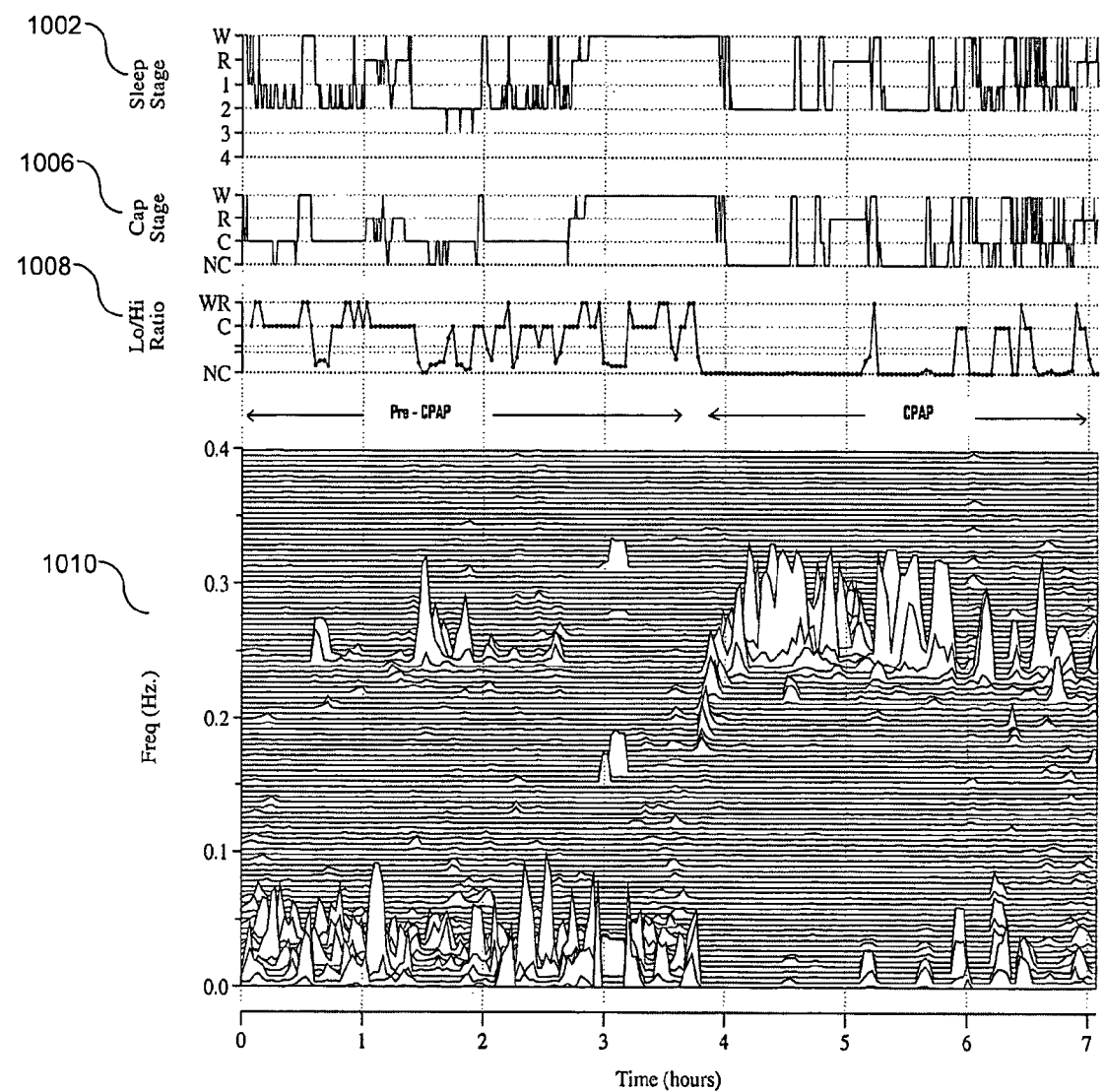
FIG. 10 illustrates detection of stable and unstable sleep using the cardiopulmonary coupling in a 56-year-old male with obstructive sleep-disordered breathing according to an embodiment of the present invention.

FIG. 10 provides an example for detecting stable and unstable sleep using the ECG-based cardiopulmonary coupling technique in a 56-year-old male with obstructive sleep-disordered breathing. The body position for the subject was supine throughout the study illustrated in FIG. 10.

Panels 1002-1010 are comparable to panels 602-610 described above with reference to FIG. 6. Panel 1002 shows conventional sleep staging, panel 1006 shows CAP staging, and panel 1008 shows low (Lo) to high (Hi) frequency coupling ratio. Panel 1010 shows the cardiopulmonary coupling spectrogram.

Alternating periods of low-frequency and high-frequency coupling that correlate with manually scored unstable (i.e., CAP) and stable (i.e., non-CAP) sleep are readily seen in FIG. 10. Continuous positive airway pressure (CPAP) therapy is applied from hour "4" onwards resulting in a clear change in physiological behavior, with a marked increase in non-CAP and in high-frequency coupling. Most of the periods scored "wake" prior to the start of therapy are actually severe sleep apnea. The high-frequency coupling observed during wake at approximately "3:00:00" is due to signal dropout from "2:55:00" to "3:15:00."

Figure 11:
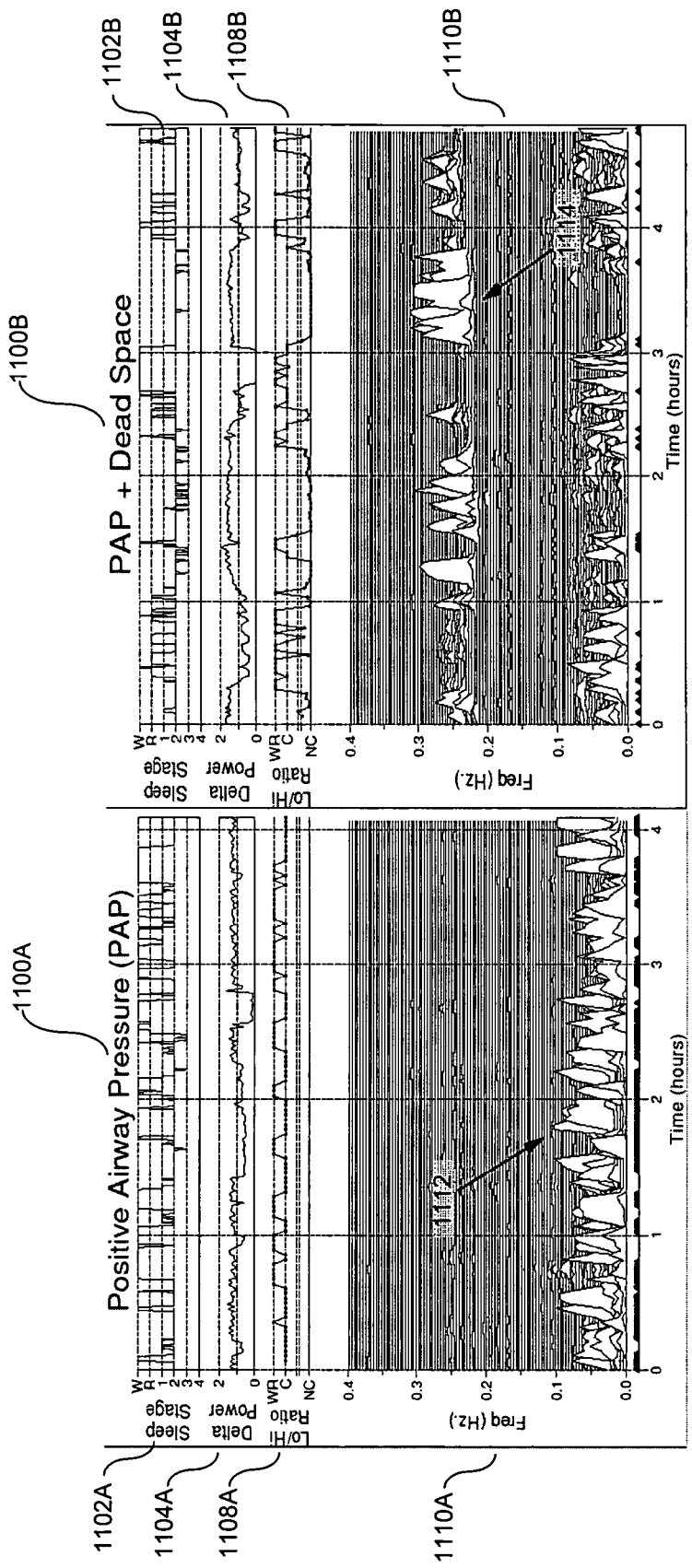
FIG. 11 illustrates a spectrographic representation of sleep-disordered breathing treated by positive airway pressure according to an embodiment of the present invention.

FIG. 11 provides an example of a spectrographic representation of sleep-disordered breathing treated by positive airway pressure. Frame 1100A shows sustained periodic breathing and predominant CAP physiology associated with low-frequency (0.01-0.1 Hz) cardiopulmonary coupling (arrow 1112) while on positive airway pressure (PAP) alone. Frame 1100B shows that the addition of 100 milliliters of dead-space to PAP using a non-vented oronasal mask and additional tubing results in a marked improvement in cardiorespiratory control evidenced by the emergence of non-CAP activity (arrow 1114) with high-frequency (0.01-0.4 Hz) cardiopulmonary coupling.

Panels 1102A-B show conventional sleep stages, and panels 1104A-B show 30-second averaged EEG delta power (μV2). Panels 1108A-B show CAP and non-CAP sleep state obtained using the ECG-derived cardiopulmonary coupling method. The spectrogram of panels 1110A-B shows the magnitude of the cardiopulmonary coupling at each frequency over the course of the study illustrated in FIG. 11. Black triangles below the spectra indicate individual periodic breathing events. These events correlate with the pathologic, sustained low-frequency cardiopulmonary coupling associated with aroused (CAP) sleep.

Thus, successful treatment of SDB is associated with a switch from low-frequency to high-frequency coupling, as seen in the above example from a combined diagnostic and therapeutic ("split" night) study (see FIG. 10). Referring to frame 1100A of FIG. 11, low-frequency coupling continues despite positive airway pressure plus oxygen therapy in a patient with congestive heart failure. Application of a technique to add physiological dead-space to positive airway pressure therapy results in the emergence of high-frequency coupling and non-CAP EEG (see frame 1100B of FIG. 11).

Therefore, cardiopulmonary coupling during sleep, as measured in accordance with the present invention, exhibits dynamic changes in health and disease, apparent as spontaneous and relatively abrupt transitions between high-frequency and low-frequency coupling regimes. The lack of overlap between the two states of stable (high-frequency coupled) and unstable (low-frequency coupled) sleep is striking (see FIGS. 6-11). Stable sleep is characterized by an absence of respiratory abnormality (or an absence of progressive flow limitation) and a presence of non-CAP EEG. On the contrary, unstable sleep is characterized by sequences of progressive flow limitation, arousals, recovery breaths, and CAP-EEG. It has been observed by the inventors that, during physiologically unstable sleep in sleep apnea, recurrent arousals induced by abnormal respiration cycles consistently generate a coupling of heart rate and ECG-derived respiration signals in the low-frequency spectrum (0.01 to 0.1 Hz) range, capturing the typical respiratory event cycle time of 20 to 100 seconds. REM sleep with severe SDB has physiological signal characteristics identical to CAP. In contrast, periods of stable breathing are associated with the non-CAP EEG pattern and high-frequency (0.1 to 0.4 Hz) coupling between respiration and beat-to-beat heart rate variability (physiologic respiratory sinus arrhythmia), reflecting the usual adult respiration rate of 8-16 breaths per minute. This stable breathing dynamic is independent of conventionally scored delta sleep or delta power.

The two states described above are not unique to SDB, but are also present in healthy subjects. While increased delta power or conventionally staged slow-wave sleep is usually associated with a non-CAP state, this association is not required as the majority of non-CAP sleep seen clinically in adults occurs in stage II sleep. Correlations of EEG power and heart rate variability dynamics have been previously described, with a clear association of increasing delta power with reduced heart rate variability. However, EEG morphologies vary significantly from individual to individual, and medication effects may introduce additional variations that increase the difficulty of accurately scoring CAP and non-CAP. The ECG-based cardiopulmonary coupling, as determined in accordance with the present invention, is computed in an automated way completely independent of EEG morphology, standard staging, or the exact morphology of the A-phase of the CAP complex. This consideration may be especially important when the EEG is altered by a drug (e.g., benzodiazepines) or disease (e.g., dementia). The presence of non-CAP behavior in subjects with low delta power (e.g., an older individual, FIG. 7), suggests that delta power processes reflect only one component of a more general process of sleep stabilizing mechanisms.

Since CAP is induced by a range of sleep-disrupting stimuli and non-CAP is a marker of sleep stability, the correlative ECG-based cardiopulmonary coupling measure can have utility in a wide range of settings using a non-intrusive, inexpensive and readily repeatable technique. These include: 1) facilitating diagnostic screening for SDB in high risk populations, tracking disease severity, following compliance with treatment, and assessing treatment effects; 2) assessing sleep quality in disorders known to have intrinsically abnormal sleep and increased CAP as a percentage of non-REM sleep, such as in primary insomnia, depression and fibromyalgia; and 3) tracking sleep quality in hostile environments, such as microgravity, in submarines, in combat, and in assessing the effect of environmental noise during sleep.

Although the ECG-based cardiopulmonary coupling measure is not a sleep stage or respiratory event detector, this technique provides a dynamic measure of cardiopulmonary coupling during sleep. Tight correlations with visually scored sleep states, therefore, would not be expected, as: 1) the time scales are different; 2) visual CAP and non-CAP rules are difficult to apply and likely imprecise at shifting boundaries of wake to sleep and non-REM to REM sleep, and during periods of switching from CAP to non-CAP; 3) severely disrupted REM sleep takes on low-frequency coupled CAP-type features; and 4) severe non-REM sleep apnea may occur in epochs scored as wake by standard criteria but detected by the present invention as an excess of power in the low-frequency range. In spite of these limitations, the reliability of ECG-based CAP detection (i.e., kappa greater than 0.75) compares favorably with what was considered excellent inter-scorer reliability (i.e., greater than 0.80) after extensive training in a recent study. However, it should be emphasized that above-described technique of cardiopulmonary coupling detection is most appropriately applied as a continuous dynamic estimator of sleep physiology rather than a "CAP scorer".

In summary, the present invention includes a spectrographic technique, derived solely from a single or dual lead ECG, which dynamically tracks changes in cardiopulmonary coupling during sleep. Spontaneous shifts are observed between high-frequency (HF) and low-frequency (LF) cardiopulmonary coupling modes during sleep in both health and disease. These two ECG-derived states have highly characteristic and predictable EEG, respiratory, and heart rate signatures, and the HF and LF states correlate with CAP/non-CAP scoring, respectively. Healthy subjects show a predominance of high-frequency coupling, while those with untreated SDB show a predominance of low-frequency coupling.

Thus, the ECG contains "hidden" information about cardiopulmonary interactions. Fourier techniques that combine analysis of beat-to-beat heart rate variability and breath-to-breath dynamics based on an ECG-derived respiration (EDR) signal can extract this information and generate a spectrogram of cardiopulmonary coupling. Besides its potential for clinical use, the results also encourage a reconsideration of sleep staging and typing in the "stability domain" that may complement traditional sleep scoring systems.

FIGS. 1-4 and 6-11 are conceptual illustrations allowing an explanation of the present invention. It should be understood that embodiments of the present invention could be implemented in hardware, firmware, software, or a combination thereof. In such an embodiment, the various components and steps would be implemented in hardware, firmware, and/or software to perform the functions of the present invention. That is, the same piece of hardware, firmware, or module of software could perform one or more of the illustrated blocks (i.e., components or steps).

Figure 5:
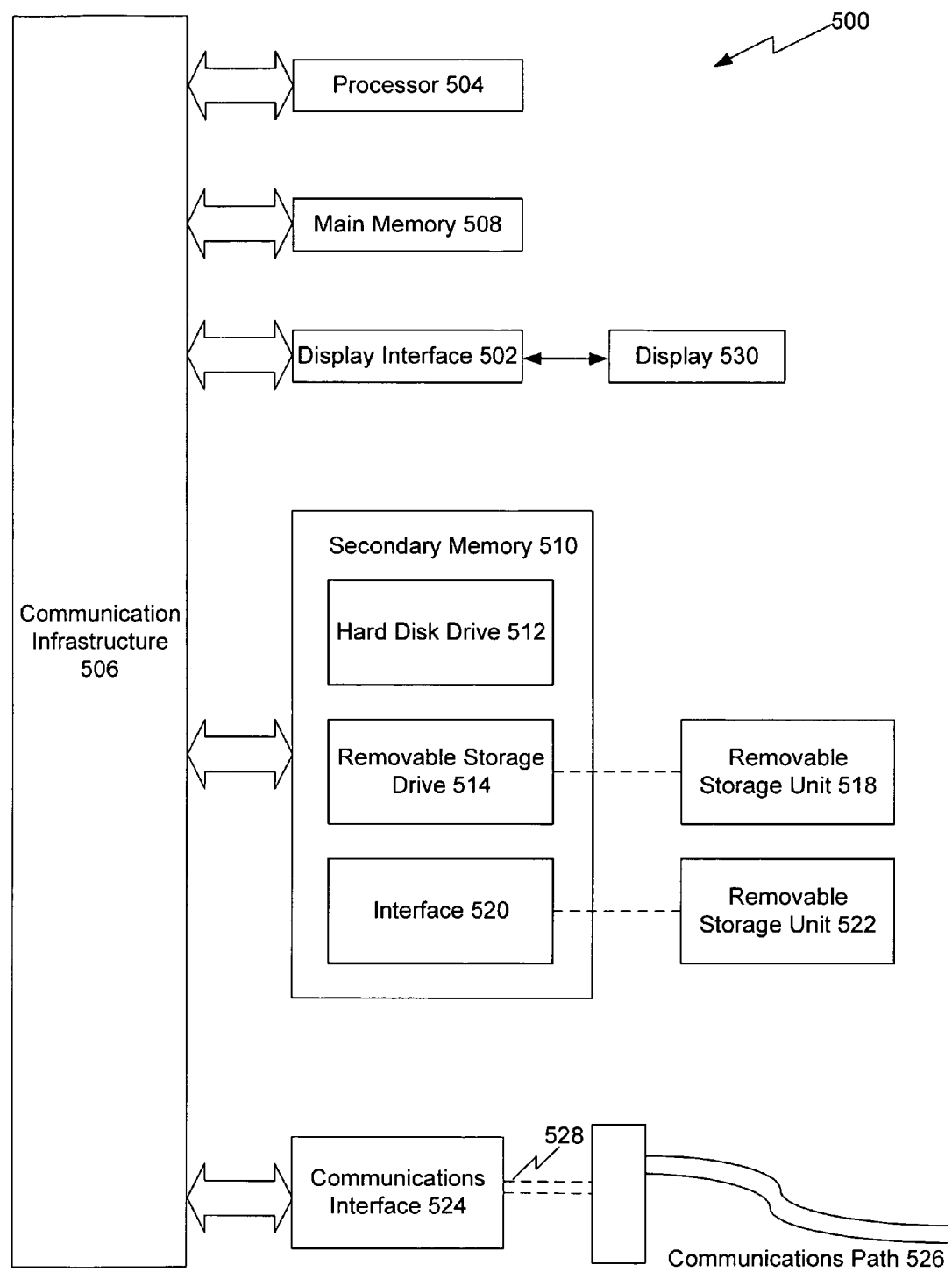
FIG. 5 illustrates an example computer system useful for implementing portions of the present invention.

The present invention can be implemented in one or more computer systems capable of carrying out the functionality described herein. Referring to FIG. 5, an example computer system 500 useful in implementing the present invention is shown. Various embodiments of the invention are described in terms of this example computer system 500. After reading this description, it will become apparent to one skilled in the relevant art(s) how to implement the invention using other computer systems and/or computer architectures.

The computer system 500 includes one or more processors, such as processor 504. The processor 504 is connected to a communication infrastructure 506 (e.g., a communications bus, crossover bar, or network).

Computer system 500 can include a display interface 502 that forwards graphics, text, and other data from the communication infrastructure 506 (or from a frame buffer not shown) for display on the display unit 530.

Computer system 500 also includes a main memory 508, preferably random access memory (RAM), and can also include a secondary memory 510. The secondary memory 510 can include, for example, a hard disk drive 512 and/or a removable storage drive 514, representing a floppy disk drive, a magnetic tape drive, an optical disk drive, etc. The removable storage drive 514 reads from and/or writes to a removable storage unit 518 in a well-known manner. Removable storage unit 518, represents a floppy disk, magnetic tape, optical disk, etc. which is read by and written to removable storage drive 514. As will be appreciated, the removable storage unit 518 includes a computer usable storage medium having stored therein computer software (e.g., programs or other instructions) and/or data.

In alternative embodiments, secondary memory 510 can include other similar means for allowing computer software and/or data to be loaded into computer system 500. Such means can include, for example, a removable storage unit 522 and an interface 520. Examples of such can include a program cartridge and cartridge interface (such as that found in video game devices), a removable memory chip (such as an EPROM, or PROM) and associated socket, and other removable storage units 522 and interfaces 520 which allow software and data to be transferred from the removable storage unit 522 to computer system 500.

Computer system 500 can also include a communications interface 524. Communications interface 524 allows software and data to be transferred between computer system 500 and external devices. Examples of communications interface 524 can include a modem, a network interface (such as an Ethernet card), a communications port, a PCMCIA slot and card, etc. Software and data transferred via communications interface 524 are in the form of signals 528 which can be electronic, electromagnetic, optical, or other signals capable of being received by communications interface 524. These signals 528 are provided to communications interface 524 via a communications path (i.e., channel) 526. Communications path 526 carries signals 528 and can be implemented using wire or cable, fiber optics, a phone line, a cellular phone link, an RF link, free-space optics, and/or other communications channels.

In this document, the terms "computer program medium" and "computer usable medium" are used to generally refer to media such as removable storage unit 518, removable storage unit 522, a hard disk installed in hard disk drive 512, and signals 528. These computer program products are means for providing software to computer system 500. The invention is directed to such computer program products.

Computer programs (also called computer control logic or computer readable program code) are stored in main memory 508 and/or secondary memory 510. Computer programs can also be received via communications interface 524. Such computer programs, when executed, enable the computer system 500 to implement the present invention as discussed herein. In particular, the computer programs, when executed, enable the processor 504 to implement the processes of the present invention, such as the various steps of methods 100, 200, 300, and 400, for example, described above. Accordingly, such computer programs represent controllers of the computer system 500.

In an embodiment where the invention is implemented using software, the software can be stored in a computer program product and loaded into computer system 500 using removable storage drive 514, hard drive 512, interface 520, or communications interface 524. The control logic (software), when executed by the processor 504, causes the processor 504 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to one skilled in the relevant art(s).

In yet another embodiment, the invention is implemented using a combination of both hardware and software.

The foregoing description of the specific embodiments will so fully reveal the general nature of the invention that others can, by applying knowledge within the skill of the art (including the contents of the documents cited and incorporated by reference herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the art.

While various embodiments of the present invention have been described above, it should be understood that they have been presented by way of example, and not limitation. It will be apparent to one skilled in the relevant art(s) that various changes in form and detail can be made therein without departing from the spirit and scope of the invention. Thus, the present invention should not be limited by any of the above-described exemplary embodiments, but should be defined only in accordance with the following claims and their equivalents.

What is claimed is:

1. A method of assessing sleep quality for a subject, wherein the method is performed in a computer-based system, comprising:
    deriving a heart rate interval series and a respiration series from at least one physiological signal obtained from the subject;
    calculating a measure of cardiopulmonary coupling, wherein the measure of cardiopulmonary coupling is computed based on the heart rate interval series and the respiration series; and
    automatically evaluating the spectral characteristics of the measure of cardiopulmonary coupling to differentiate between an obstructive sleep disorder and a non-obstructive sleep disorder.

2. The method according to claim 1, wherein said evaluating step comprises:
    identifying at least one of a plurality of spectral peaks and broad coupling spectra to detect said obstructive sleep disorder.

3. The method according to claim 1, wherein said evaluating step comprises:
    identifying at least one of a single dominant frequency and a narrow spectral dispersion to detect said non-obstructive sleep disorder.

4. The method according to claim 1, wherein said evaluating step is independent of polysomnogram scoring.

5. The method according to claim 1, further comprising:
    producing a graphical representation of said cardiopulmonary coupling.

6. The method according to claim 5, further comprising:
    automatically evaluating said graphical representation to detect a CAP state, a non-CAP state, a wake state, or an REM state.

7. The method according to claim 5, wherein 30-second epochs are applied to the graphical representation to thereby detect a CAP state, a non-CAP state, a wake state, or an REM state.

8. The method according to claim 5 further comprising:
    automatically evaluating the graphical representation of said cardiopulmonary coupling to detect at least one of an aging or pathological condition.

9. The method according to claim 1, further comprising:
    automatically determining an effect of a drug or non-pharmacologic intervention.

10. The method according to claim 1, further comprising:
    automatically determining an adverse or therapeutic effect of a drug or non-pharmacologic intervention.

11. The method according to claim 1, wherein the respiration series is derived from an electrocardiogram signal.

12. The method according to claim 1, wherein the heart rate series and the respiration series are each derived from different physiological signals.

13. The method according to claim 1, wherein the physiological signal is obtained using an electrocardiogram.

* * * * *